US011448653B2

(12) United States Patent
Evans et al.

(10) Patent No.: US 11,448,653 B2
(45) Date of Patent: *Sep. 20, 2022

(54) HIGH PRESSURE SPERM SORTING AND FLOW CYTOMETER METHODS

(71) Applicant: Inguran, LLC, Navasota, TX (US)

(72) Inventors: Kenneth Michael Evans, College Station, TX (US); Thomas Boyd Gilligan, College Station, TX (US); Richard W. Lenz, Eastman, WI (US); Ramakrishnan Vishwanath, Hamilton (NZ); Clara Gonzalez-Marin, College Station, TX (US)

(73) Assignee: Inguran, LLC, Navasota, TX (US)

( * ) Notice: Subject to any disclaimer, the term of this patent is extended or adjusted under 35 U.S.C. 154(b) by 179 days.

This patent is subject to a terminal disclaimer.

(21) Appl. No.: 16/806,853

(22) Filed: Mar. 2, 2020

(65) Prior Publication Data

US 2020/0200762 A1 Jun. 25, 2020

Related U.S. Application Data

(63) Continuation of application No. 14/045,617, filed on Oct. 3, 2013, now Pat. No. 10,620,213, which is a continuation-in-part of application No. PCT/US2013/028931, filed on Mar. 4, 2013, and a continuation-in-part of application No. PCT/US2013/028934, filed on Mar. 4, 2013.

(60) Provisional application No. 61/710,343, filed on Oct. 5, 2012.

(51) Int. Cl.
*G01N 33/58* (2006.01)
*G01N 33/50* (2006.01)
*G01N 15/14* (2006.01)
*G01N 33/52* (2006.01)
*C12N 5/071* (2010.01)
*C12N 5/076* (2010.01)
*G01N 15/10* (2006.01)

(52) U.S. Cl.
CPC .......... *G01N 33/582* (2013.01); *C12N 5/061* (2013.01); *C12N 5/0612* (2013.01); *G01N 15/1425* (2013.01); *G01N 15/1459* (2013.01); *G01N 33/5005* (2013.01); *G01N 33/52* (2013.01); *G01N 2015/1006* (2013.01); *G01N 2015/149* (2013.01); *G01N 2015/1415* (2013.01)

(58) Field of Classification Search
CPC ......... G01N 33/582; G01N 2015/1006; G01N 2015/149; C12N 5/061; C12N 5/0612
See application file for complete search history.

(56) References Cited

U.S. PATENT DOCUMENTS

| | | |
|---|---|---|
| 5,135,759 A | 8/1992 | Johnson |
| 6,149,867 A | 11/2000 | Seidel et al. |
| 6,263,745 B1 | 7/2001 | Buchanan et al. |
| 6,524,860 B1 | 2/2003 | Seidel et al. |
| 7,371,517 B2 | 5/2008 | Evans et al. |
| 7,758,811 B2 | 7/2010 | Durack et al. |
| 7,799,569 B2 | 9/2010 | Durack et al. |
| 7,838,210 B2 | 11/2010 | Ludwig et al. |
| 7,838,509 B2 | 11/2010 | Ellington et al. |
| 2005/0003472 A1 | 1/2005 | Anzar et al. |
| 2005/0244805 A1 | 11/2005 | Ludwig et al. |
| 2006/0067916 A1 | 3/2006 | Schenk et al. |
| 2006/0121440 A1 | 6/2006 | Schenk et al. |
| 2007/0117086 A1 | 5/2007 | Evans et al. |
| 2009/0053821 A1 | 2/2009 | Laikhter et al. |
| 2009/0176271 A1 | 7/2009 | Durack et al. |
| 2009/0208977 A1 | 8/2009 | Hudson et al. |
| 2011/0004052 A1* | 1/2011 | Schenk ................. A01N 1/021 600/35 |
| 2011/0076712 A1 | 3/2011 | Gilligan |
| 2011/0236923 A1 | 9/2011 | Hashemi |
| 2013/0084558 A1 | 4/2013 | Evans |
| 2014/0099627 A1 | 4/2014 | Gilligan et al. |
| 2014/0099628 A1 | 4/2014 | Evans et al. |

FOREIGN PATENT DOCUMENTS

| | | |
|---|---|---|
| WO | 9905504 A2 | 2/1999 |
| WO | 1999005504 A2 | 2/1999 |
| WO | 2001037655 A1 | 5/2001 |
| WO | 0151612 A1 | 7/2001 |
| WO | 200185913 A2 | 11/2001 |
| WO | 2004012837 A3 | 2/2004 |
| WO | 2004104178 A1 | 12/2004 |
| WO | 2005095960 A1 | 10/2005 |
| WO | 2009031831 A2 | 3/2009 |
| WO | 2010021627 A1 | 2/2010 |
| WO | 2011/123166 A2 | 10/2011 |
| WO | 2012014142 A1 | 2/2012 |

(Continued)

OTHER PUBLICATIONS

Brazilian Office Action dated Mar. 20, 2020 issued in related BR Appl. No. BR112015007481-2.
European Office Action dated Apr. 15, 2020 issued in related EP Appl. No. 13843780.1.
Brazilian Office Action dated Apr. 1, 2020 issued in related BR Appl. No. BR122016004716-4.

(Continued)

*Primary Examiner* — Lynn Y Fan
(74) *Attorney, Agent, or Firm* — Ryan Christensen; Hashim Rahman

(57) ABSTRACT

Cell sorting methods that improve sorting efficiency and productivity by elevating sorting pressures and incorporate certain steps to help the cells better survive such elevated pressures. In the case of sperm, sorting the steps of standardizing sperm samples, staining sperm samples in a single step, calibrating a flow cytometer to place sperm in the leading edge of droplets, and changing a catch fluid distance may be incorporated individually, or in combination to help sperm better survive the sex sorting process.

14 Claims, 6 Drawing Sheets

(56) References Cited

FOREIGN PATENT DOCUMENTS

| WO | 2012167151 A1 | 12/2012 |
|---|---|---|
| WO | 2013049631 A1 | 4/2013 |

OTHER PUBLICATIONS

Rens, Wim, et al. "Improved Flow Cytometric Sorting of X- and Y-Chromosome Bearing Sperm: Substantial Increase in Yield of Sexed Semen " Molecular Reproduction and Development 52:50-56 (1999).
European Search Report dated Jan. 29, 2016 issued in related EP Appl. No. 15186997.1.
Filho, M. et al. "Sex-Sorted Sperm for Artificial Insemination and Embryo Transfer Programs in Cattle." Anim. Reprod., v.11, n.3, p. 217-224, Jul./Sep. 2014.
Gaviraghi, A. et al. "Minimum Number of Spermatozoa Per Dose in Mediterranean Italian Buffalo {Bubalus Bubalis) Using Sexed Frozen Semen and Conventional Artificial Insemination." Theriogenology 79 (2013) 1171-1176.
Kline, P. et al. "Insemination with Sex Sorted Fresh Bovine Spermatozoa Processed in the Presence of Antioxidative Substances." Reprod Dom Anim 42, 58-62 (2007).
Vishwanath, R. "Sexed Sperm Vs Conventional Sperm—A Comparative Discussion." Proceedings, Applied Reproductive Strategies in Beef Cattle• Aug. 17 &18, 2015. http://appliedreprostrategies.com/2015/documents/proceedings/16bVishwanath-pg250-256 .pdf.
European Search Report dated Feb. 5, 2016 issued in related EP Appl. No. 13844253.8.
Henkel, Rolf, "Sperm Preparation: State-of-the-Art-Physiological Aspects and Application of Advanced Sperm Preparation Methods." Asian Journal of Andrology, vol. 14, No. 2, Mar. 1, 2012.
New Zealand Notice of Acceptance dated Apr. 20, 2016 in related NZ Appl. No. 630380.
U.S. Office Action dated Jan. 8, 2016 issued in related U.S. Appl. No. 13/784,578.
Australian Examination Report dated Aug. 30, 2016 issued in related NZ Appl. No. 2013327057.
Canadian Office Action dated Sep. 26, 2016 issued in related CA Appl. No. 2,886,796.
Australian Examination Report dated Apr. 18, 2016 issued in related NZ Appl. No. 2013325223.
Australian Examination Report dated Sep. 13, 2016 issued in related NZ Appl. No. 2013325223.
Canadian Office Action dated Sep. 26, 2016 issued in related CA Appl. No. 2,886,782.
U.S. Office Action dated Oct. 21, 2016 issued in related U.S. Appl. No. 13/784,597.
Australian Examination Report dated Jun. 10, 2016 issued in related NZ Appl. No. 2013325222.
Canadian Office Action dated Sep. 26, 2016 issued in related CA Appl. No. 2,886,903.
U.S. Office Action dated Oct. 11, 2016 issued in related U.S. Appl. No. 14/861,572.
New Zealand Notice of Acceptance dated Nov. 7, 2016 in related NZ Appl. No. 630388.
U.S. Office Action dated Nov. 21, 2016 issued in related U.S. Appl. No. 13/784,578.
New Zealand Notice of Acceptance dated Nov. 16, 2016 in related NZ Appl. No. 630394.
Australian Examination Report dated Nov. 24, 2016 issued in related AU Appl. No. 2016231560.
Australian Examination Report dated Dec. 15, 2016 issued in related AU Appl. No. 2013327057.
Paulenz et al. "Comparison of Fertility Results after Vaginal Insemination Using Different Thawing Procedures and Packages for Frozen Ram Semen." Acta Veterinaria Scandinavica 2007, 49:26, 7 pages.
U.S. Office Action dated Mar. 29, 2017 in related U.S. Appl. No. 14/861,572.
Amirat et al. "Modifications of Bull Spermatozoa Induced by Three Extenders: Biociphos, Low Density Lipoprotein and Triladyl, Before, During and Aller Freezing and Thawing." Reproduction (2005), v129, p. 535-543.
Kornhauser et al. "Applications of Hydroxy Acids: Classification, Mechanisms, and Photoactivity. Clinical.", Cosmetic and Investigational Dermatology (2010), v3, p. 135-142.
U.S. Office Action dated Mar. 16, 2017 in related U.S. Appl. No. 14/784,578.
EP Examination Report dated Mar. 20, 2017 in related EPAppl. No. 13843780.1.
EP Examination Report dated May 8, 2017 in related EPAppl. No. 15186997.1.
AU Notice of Acceptance dated Mar. 24, 2017 in related AU Appl. No. 2013327057.
U.S. office Action dated Sep. 25, 2017 issued in related U.S. Appl. No. 14/861,572.
Juengel et al. Reproduction in Domestic Ruminants VIII (Aug. 2014), i-vi (Year: 2014).
Fouz et al. Factors associated with 56-day non-return rate in dairy cattle. Pesq. agropec. bras., Brasilia (2011), v46(6), (Year: 2011).
De Graaf et al. Reproduction in Domestic Ruminants VIII (Aug. 2014), p. 507-522 (Year: 2014).
U.S. office Action dated Oct. 6, 2017 issued in related U.S. Appl. No. 14/784,578.
Canadian office Action dated Sep. 18, 2017 issued in related CA Appl. No. 2,886,782.
Australian office Action dated Sep. 18, 2017 issued in related AU Appl. No. 2015230805.
U.S. office Action dated Aug. 22, 2017 issued in related U.S. Appl. No. 13/784,597.
Shapiro, Howard M. Section 6.8 of "Practical Flow Cytometry", Fourth Edition. 2003. pp 268-271.
European examination report dated Feb. 2, 2018 in related EP application No. 13844253.8.
U.S. Office Action report dated Mar. 13, 2018 in related U.S. Appl. No. 14/861,572.
Australian Notice of Acceptance dated Mar. 14, 2018 in related AU application No. 2015230805.
U.S. Office Action report dated Mar. 13, 2018 in related U.S. Appl. No. 13/784,578.
Australian Notice of Acceptance dated Apr. 15, 2018 in related AU application No. 2017201275.
EP Examination Report dated Jun. 19, 2 018 in related EPAppl. No. 15186997.1.
U.S. Office Action dated Jun. 1, 2018 in related U.S. Appl. No. 13/784,597.
Canadian Requisition by the Examiner dated Aug. 27, 2018 issued in related CA Appl. No. 2,886,782.
Canadian Requisition by the Examiner dated Aug. 10, 2018 issued in related CA Appl. No. 2,886,903.
Carvalho, J.O., et al.; "Quality Assessment of Bovine Cryopreserved Sperm After Sexing by Flow Cytometry and Their Use in in vitro Embryo Production"; Article, 2010, pp. 1521-1530, vol. 74, Theriogenology USA (10 pages).
Frijters, A.C.J., et al.; "What Affects Fertility of Sexed Bull Semen More, Low Sperm Dosage or the Sorting Process?"; Article, 2009, pp. 64-67; vol. 71, Theriogenology, USA (4 pages).
Klinc, Primoz; "Improved Fertility of Flowcytometrically Sex Selected Bull Spermatozoa"; Inaugural-Dissertation; 2005, pp. 1-108, Aus dem Institut fur Tierzucht Mariensee, Hannover (108 pages).
Long, C.R., et al.; "Effect of Flow Cytometric Sperm Sorting Parameters on Porcine Oocyte Penetration and 4 Developmental Competence"; Article, pp. 1-24, U.S. Department of Agriculture, Agricultural Research Service, ☐ Beltsville, MD USA (24 pages).
milkproduction.com; "Sexed Semen: Is ii Finally a Reality?"; http://www.milkproduction.com/Library/Scientific-articles/Reproduction/Sexed-semen-Is-ii/; Dec. 18, 2008 (4 pages).
Suh, T.K., et al.; "Pressure During Flow Sorting of Bull Sperm Affects Post-Thaw Motility Characteristics"; Abstract Only; p. 516, Fort Collins, CO USA (1 page).

(56) References Cited

OTHER PUBLICATIONS

Seidel et al. Current status of sexing mammalian spermatozoa. Reproduction. 2002;124:733-743.
Suh, T.K., et al., "High pressure flow cytometric sorting damages sperm", Theriogenology vol. 64, Issue 5, pp. 1035-1048, 2005.
PCT Search Report and Written Opinion dated Apr. 22, 2014, issued in corresponding PCT Application No. PCT/US13/63286 (24 pp).
Burroughs, C.A.,"Sex-Sorting of Bovine Sperm" Thesis-Colorado State University-Depailmentof Biomedical Sciences (2011) 86 pp.
De Graaf, S.P., et al., "Application of seminal plasma in sex-sorting and sperm cryopreservation", Theriogenology 70 (2008)1360-1363.
De Graaf, S.P., et al., "Birth of offspring of pre-determined sex after artificial insemination of frozen-thawed, sex-sorted and re-frozen-thawed ram spermatozoa", Theriogenology 67 (2007) 391-398.
Garcia, E.M., et al. "Improving the fertilizing ability of sex sorted boar spermatozoa", Theriogenology 68 (2007) 771-778.
Presicce, G.A., et al., "First Established Pregnancies in Mediterranean Italian Buffaloes (*Bubalus bubalis*) following Deposition of Sexed Spermatozoa near the Utero Tubal Junction", Reproduction in Domestic Animals 40.1 (2005): 73-75.
Strober, Warren. "Trypan blue exclusion test of cell viability", Current protocols in immunology (2001 }: A-38.
"Characteristics of Deionised Water", 2004.
US FDC, Fooo Color Facts. 2007.
Stap et al., "Improving the Resolution of Cryopreserveo X- and Y-Sperm During DNA Flow Cytometfic Analysis with the Addition of Per-coll to Quench the Fluorescence of Dead Sperm" J. Anim. Sci, 1998, 76, 1896-1902.
Seidel, G.E., Jr., "Sperm sexing technology—The transition to commercial app!lcation—An introduction to the symposium "Update on sexinf! mammalian sperm"", Thenogenolgy ?•J (2009) 1-3.
U.S. Office Action dated Jul. 18, 2014, issued 111 corr-espondinfJ U.S. Appl. No. 13/784,578 (21 pp).
Lardy, et al., {1943). "Effect of pH ano certain electrolytes on the metabolism of ejaculated spermatozoa". Arn. J. Physiol, 138. 741-746.
Johns!. et al.. "Fluorescence Quenching of Tris(2,2'-bipyridine)Ruthenium(l!) Dichloride by Certain Orfianic Dyes", Journal of Solution Chemistry, Oct. 20"!0, vol. 39, Issue 10, pp. 1520-1530.
U.S. office Action for related U.S. Appl. No. 13/784,578, dated Dec. 26, 2014.
U.S. office Action for related U.S. Appl. No. 13/784,597, dated Jan. 14, 2015.
Underwood et al. "In vitro characteristics of frozen-thawed, sex-sorted bull sperm after refreezing or incubation at 15 or 37° C." Theriogenology (2009) 72: 1001-1008).
Hilinshead et al. "Birth of lambs of a pre-determined sex after in vitro production of embryos using frozen-thawed sex-sorted and re-frozen-thawed ram spermatozoa" Reproduction (2004) 127: 557-568.
Johnson et al., "Improved Flow Sorting Resolution of X- & Y-Chromosome Bearing Viable Sperm Separation Using Dual Staining and Dead Cell Gating." Cytometry, vol. 17, Supplement 7, Abstract, p. 83 (1994).
International Search Report dated Apr. 22, 2013 in related PCT Appl. No. PCT/US13/63286.
International Search Report dated May 21, 2013 in related PCT Appl. No. PCT/US13/28934.
Australian Patent Examination Report dated Sep. 22, 2015 in related AU Appl. No. 2013325223.
New Zealand Patent Examination Report dated Sep. 17, 2015 in related NZ Appl. No. 630380.
New Zealand Patent Examination Report dated Sep. 17, 2015 in related NZ Appl. No. 630388.
New Zealand Patent Examination Report dated Sep. 17, 2015 in related NZ Appl. No. 630394.

U.S. office Action dated Aug. 13, 2015 in related U.S. Appl. No. 13/784,578.
Schenk et al. "Pregnancy Rates in Heifers and Cows with Cryopreserved Sexed Sperm: Effects of Sperm Numbers Der Inseminate, Sorting Pressure and Sperm Storage before Sorting." Theriogenology, 71, 2009, p. 717-728.
DeJamette et al. "Evaluating the Success of Sex-Sorted Semen in US Dairy Herds From on Farm Records." Theriogenology, 71, 2009, p. 49-58.
DeJamette et al. "Effects of 2.1 and 3.5 × 106 Sex-Sorted Sperm Dosages on Conception Rates of Holstein Cows and Heifers" J_ Dairy Sci. 93, p. 4079-4085. 2010.
DeJamette et al. "Effects of Sex-Sorting and Sperm Dosage on Conception Rates of Holstein Heifers: Is Comparable Fertility of Sex-Sorted and Conventional Semen Plausible?" J_ Dairy Sci. 94, p. 3477-3483. 2011.
Frijters et al. "What Affects Fertility of Sexed Bull Semen More, Low Sperm Dosage or the Sorting Process." Theriogenology, 71, 2009, p. 64-67.
Featured Charter Sponsor—Dairy Cattle Reproduction Council. 2014. http://www.dcrcouncil.org/newsletters/2014-march/featured-charter-sponsor.aspx.
BO. BO Influx cell sorter user's guide. BO. 2011 ;1-378.
European Search Report dated May 17, 2 016 issued in related EP Appl. No. 13844269.4.
Canadian Office Action dated Jan. 18, 2016 issued in related CA Appl. No. 2,886,796.
New Zealand Examination Report dated Jan. 21, 2016 issued in related NZ Appl. No. 630394.
U.S. Office Action dated Jan. 11, 2016 issued in related U.S. Appl. No. 13/784,597.
New Zealand Examination Report dated Jan. 20, 2016 issued in related NZ Appl. No. 630388.
Canadian Office Action dated Jan. 18, 2016 issued in related CA Appl. No. 2,886,782.
European Search Report dated Feb. 22, 2016 issued in related EP Appl. No. 13843780.1.
Johnson, L., et al. "The Beltsville Sperm Sexing Technology: High-Speed Sperm Sorting Gives Improved Sperm Output for In Vitro Fertilization and AI." J_ Anim. Sci. vol. 77, Suppl. 2/J_ Dairy Sci. vol. 82, Suppl. Feb. 1999.
Johnson, L., et al. "Preselection of Sex of Offspring in Swine for Production: Current Status of the Process and its Application." Theriogenology 63 (2005) 615-624.
Brazilian Office Action dated Oct. 6, 2020 issued in related BR Appl. No. BR112015007481-2.
Indian Office Action dated Dec. 27, 2018 is related IN Appl. No. 951/KOLNP/2015.
European Search Report dated Mar. 13, 2019 is related EP Appl. No. 19153112.8.
U.S. Office Action dated Mar. 22, 2019 is related U.S. Appl. No. 14/861,572.
European Examination Report dated May 16, 2019 issued in related EP Appl. No. 15186997.1.
Chinese Office Action dated Feb. 19, 2 019 issued in related CN Appl. No. 20150827567.0.
European Extended Search Report dated Mar. 13, 2019 issued in related EP Appl. No. 19153112.8.
Brazilian Office Action dated Apr. 22, 2019 issued in related BR Appl. No. 112015007479-0.
Brazilian Office Action dated Apr. 22, 2019 issued in related BR Appl. No. 112015007480-4.
U.S. Final Office Action dated Mar. 22, 2019 issued in related U.S. Appl. No. 14/861,572.
United States Office Action dated May 17, 2019 issued in related U.S. Appl. No. 131784,578.
Gardner et al. Effect on Semen Dilution on Bovine Sperm Viability as Determined by Dual-DNA Staining and Flow Cytometry.Journal of Andrology, 18(3), 324-331. (Year: 1997).

\* cited by examiner

FIG. 7A
FIG. 7B
FIG. 7C
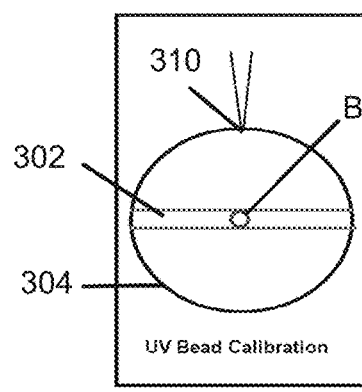
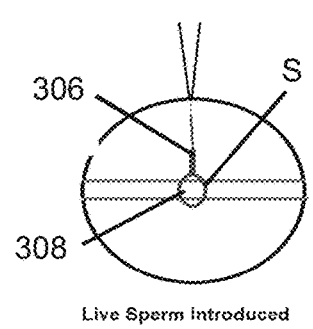
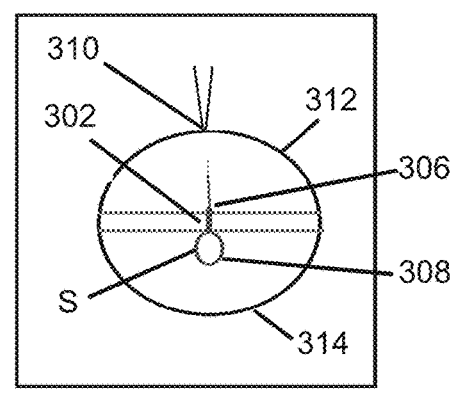

HIGH PRESSURE SPERM SORTING AND FLOW CYTOMETER METHODS

This application is a Continuation of U.S. patent application Ser. No. 14/045,617 filed on Oct. 3, 2013, which is a Continuation in Part of International Application No. PCT/US2013/028934, filed Mar. 4, 2013, a Continuation in Part of International Application No. PCT/US2013/028931, filed Mar. 4, 2013, and claims the benefit to U.S. Provisional Patent Application No. 61/710,343 filed on Oct. 5, 2012, the entire contents of each of which are incorporated herein by reference.

TECHNICAL FIELD

Generally, this disclosure relates to cell sorting methods, and more particularly relates to sperm sorting methods and flow cytometer methods that improve the efficiency and recovery associated with sex sorting sperm.

BACKGROUND

The most widely used sperm sorting methods rely on the detection of quantifiable differences in the DNA content of X-chromosome bearing sperm and Y-chromosome bearing sperm. Various modifications to flow cytometers for this purpose are described in U.S. Pat. Nos. 5,135,759, 6,263,745, 7,371,517 and 7,758,811, each of which are incorporated herein by reference. In many species, the difference in DNA content can be small. In bovine, for example, Holstein bulls have about a 3.8% difference in DNA content, while Jersey bulls have about a 4.1% difference. The inexact nature of stoichiometric DNA staining makes these minor variations difficult to ascertain.

While the fluorescent dye Hoechst 33342 is suitable for distinguishing such variations in non-toxic concentrations, sperm must be incubated at elevated temperatures and at an elevated pH for Hoechst 33342 penetration to provide uniform staining. Sperm are delicate cells in nature, as they lack the capacity to replicate and have a short life span. As such, injuries imposed by each of elevating sperm temperature and changing the sperm pH may result in a significant detriment to sperm health. Additionally, the pressure and sheering forces applied to sperm within a flow cytometer may further compromise sperm membranes. These factors accelerate the deterioration of sperm membranes further reducing the already limited shelf life of viable sperm for use in artificial insemination or other assisted reproductive procedures.

Accordingly, previous sperm sorting efforts focused on utilizing smaller insemination samples and producing the greatest amount of sorted sperm in the shortest amount of time. U.S. Pat. No. 6,149,867, incorporated herein by reference, describes methods and devices geared towards helping sperm better survive flow cytometric sorting in combination with reduced dosage inseminates. Subsequent advances in flow sorting focused on improvements in detection or throughput. However, as speeds and throughputs increased, larger quantities of sperm, including viable sperm of the desired sex, are discarded with waste. Additional tradeoffs between purity and recovery also exist. For example, where the desirable purity is greater than 95%, fewer sperm can be sex sorted with the requisite confidence level as compared to purities of 70%, 80% or even 90%. Meaning, fewer sperm are recovered at increasingly high purities and that more viable sperm are disposed with the waste stream.

Additional losses in efficiency exist as a consequence of discarding viable sperm due to the occurrence of coincident events. A coincident event occurs when two or more sperm are too close together to be separated. In such an event, all of coincident sperm may be discarded with waste, whereas some or all of those discarded cells may have been desirable to collect.

Previously, recovery problems were often overlooked, or moot, in view of raw flow sorting throughput. Bovine sperm, for example, is relatively easy to collect and process and high purities may be desirable in both the beef and dairy industries, even at the expense of discarding as much as about 90% of the sperm. However, this high throughput methodology is not acceptable for sperm in limited supply. For example, a specific animal could possess exceptionally desirable genetic qualities, but may produce poor sperm samples for sorting. A species could be rare, endangered, or difficult to collect, limiting the amount of sperm available for sorting. A previously collected sample may be preserved, but the animal or species may no longer be available for subsequent collections. Regardless of the circumstances, the wasteful sperm sorting process is undesirable for sperm in limited supply or sperm with high value. A need, therefore, exists for a method of sorting viable sperm with an improved efficiency in recovering sperm.

Additional limitations in convention sorting technology exist due to sperm damage produced during the staining and other processing stages. Even operational parameters of the flow cytometer instrument itself can introduce or exacerbate damage to relatively delicate sperm. Until a point of over staining is reached, generally higher pHs and longer staining times increase the uniformity with which dye associates with nuclear DNA allowing for a better distinction between X-chromosome bearing sperm and Y-chromosome bearing sperm. However, the overall health of sperm degenerates quickly with the elevated temperatures or an elevated pH. At a point, any additional resolution gained by extending staining time is lost due to the number of sperm that either die or become unviable.

In addition to the injuries caused by upfront handling or staining, the sorting process itself imposes pressures and stresses on sperm which have been reported as detrimental to sperm health. In particular, flow cytometer operating pressures of 50 psi (pounds per square inch), or approximately $3.45 \times 10^5$ Pascal, have been documented as damaging sperm in the sorting process. *High pressure flow cytometric sorting damages sperm*, Theriogenology 2005 Sep. 15:64(5) 1035-48. Accordingly, the industry standard has been to sort sperms at operating pressure less than 50 psi.

SUMMARY OF THE INVENTION

Certain embodiments of the claimed invention are summarized below. These embodiments are not intended to limit the scope of the claimed invention, but rather serve as brief descriptions of possible forms of the invention. The invention may encompass a variety of forms which differ from these summaries.

One embodiment relates to a method of sorting sperm which may begin with obtaining a sperm sample. The sperm sample may be stained with a DNA selective dye and a quenching dye in a single dilution. The stained sperm may be sorted in a flow cytometer at an elevated pressure, where additional damaged imposed on the sperm by the elevated pressure is reduced by the step staining the sperm in a single dilution.

Another embodiment relates to a method of sorting sperm which may begin with obtaining a sperm sample. The sperm may be stained with a DNA selective dye and used to calibrate a flow cytometer. The flow cytometer may be calibrated so that the heads of the live sperm tend to be placed in the leading edge of droplets formed by the flow cytometer and then sperm are sorted with the calibrated flow cytometer.

BRIEF DESCRIPTION OF THE DRAWINGS

FIGS. 7A-7C illustrates the position of beads (B) or sperm (S) in droplets formed by a flow cytometer.

Figure 1:
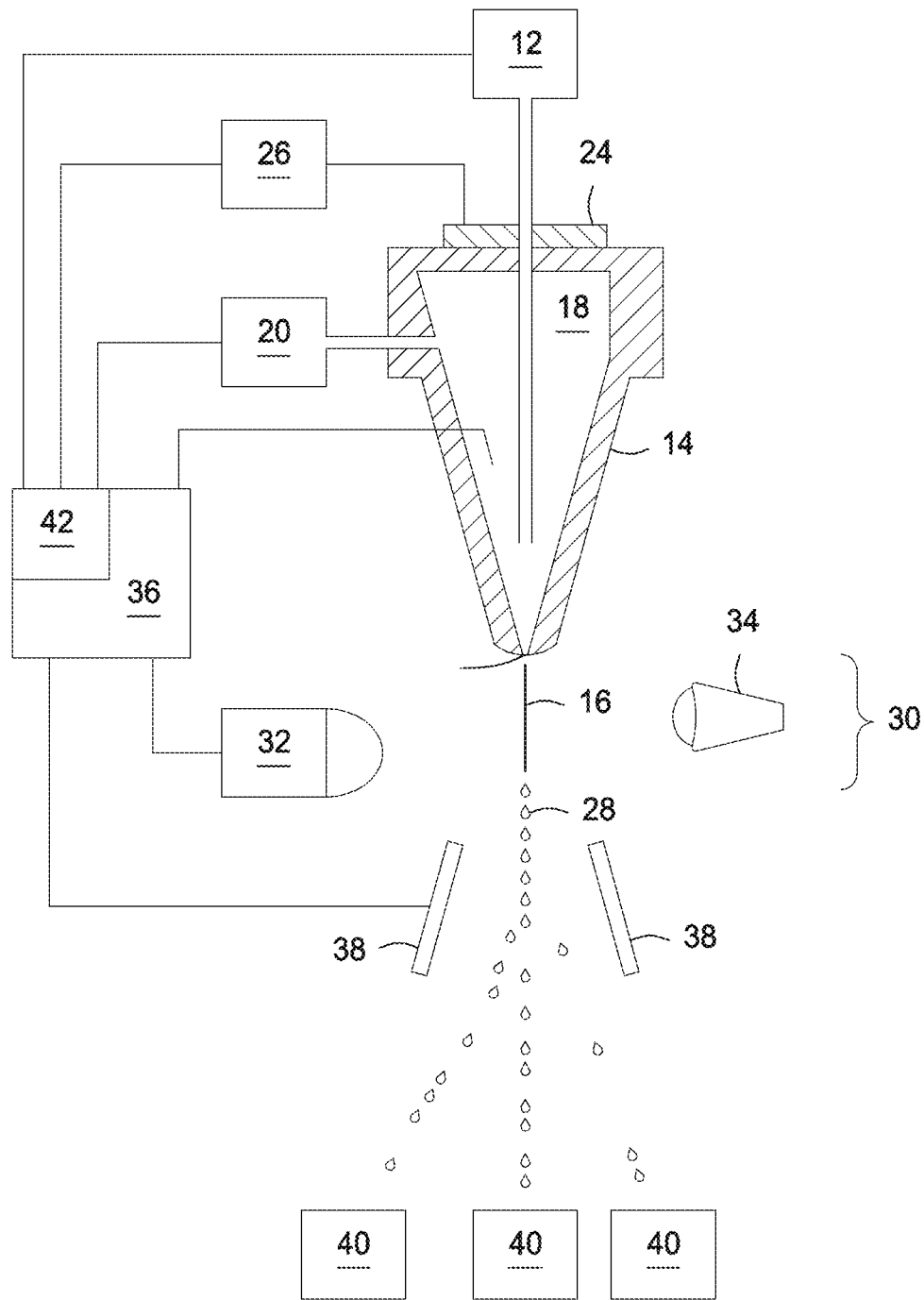
FIG. 1 illustrates a schematic of a flow cytometer for sorting sperm in accordance with certain embodiments described herein.

While the present invention may be embodied with various modifications and alternative forms, specific embodiments are illustrated in the figures and described herein by way of illustrative examples. It should be understood the figures and detailed descriptions are not intended to limit the scope of the invention to the particular form disclosed, but that all modifications, alternatives, and equivalents falling within the spirit and scope of the claims are intended to be covered.

MODES FOR CARRYING OUT THE INVENTION

As used herein, the term "instrument parameter" should be understood to include settings relating to the analyzing and/or sorting conditions in, of, and relating to an instrument, where such settings may be modified by manual or automatic adjustments to the instrument. In the case of a flow cytometer, or other similar instruments, the instrument parameters may include, sample pressure, sample flow rate, sheath fluid pressure, sheath flow rate, drop drive frequency, drop drive amplitude, coincidence abort logic, gating regions, sorting logic, and other similar settings.

The term "sorting parameters" may include those conditions relating to sorting preformed in a particle sorting instrument. Sorting parameters may include measured sorting parameters in addition to parameters which are determined offline, estimated by an operator, and conditions relating to a sorted population of particles or cells.

"Measured sorting parameters" may include those conditions relating to sorting measured directly, calculated, or determined in a particle sorting instrument while analyzing and/or sorting a population of particles or cells. In the case of a flow cytometer, or other similar instruments, the measured sorting parameters may include: event rate; sort rate; sorting efficiency; abort rate; dead gate percentage; live oriented gate percentage; valley to peak ratio; or the percentage of events in other sorting gates, such as an X-sort gate or a Y-sort gate.

As used herein the term "coincidence event" may be understood as a single event in a particle sorting instrument where one or more particles or cells are too close to be separated for individual collection, and where only one of the two cells or particles is desirable for collection. In the case of a droplet sorting jet-in-air flow cytometer, a coincident event may occur when two sperm are close enough such that they will end up in the same droplet but only one of those two cells is desired for collection.

The term "sorting efficiency" may be understood to refer to the recovery of particles or cells in terms of the percentage of particles or cells sorted or collected out of a group of cells or particles which are analyzed. The analyzed group of cells may be the total number of cells analyzed or may be a subset of the total number of cells analyzed, such as the analyzed cells determined to be viable or otherwise desirable for analysis and potential collection.

With respect to sorting, the term "productivity," as used herein may be understood to refer to the number of sorted or collected particles or cells per unit time.

With respect to sorting, the term "purity" may refer to an actual or estimated percentage of cells or particles in the population of collected or sorted particles or cells having the characteristic for which the particles were sorted. In the case of sperm, purity may refer to the percentage of X-chromosome bearing sperm in a population sorted for X-chromosome bearing sperm or the percentage of Y-chromosome bearing sperm in a population sorted for Y-chromosome bearing sperm regardless of the viability of the sorted sperm.

Certain aspects disclosed herein relate to a method of efficiently sorting a sperm sample in a particle sorting instrument, however, the methods described are not limited to any specific instruments. Particle sorting instruments may include jet-in-air flow cytometers, such as the Legacy MoFlo® SX, MoFlo® XDP (Beckman Coulter, Miami Fla., USA); however, other commercially available flow cytometers could be modified for sperm sorting as well. The jet-in-air flow cytometers may be outfitted with orienting features such as, orienting nozzles for orienting sperm, optics for uniformly illuminating cells, and/or radially uniform optics for collecting fluorescence emissions from all cells regardless of their orientation. Cytometers having different flow chambers may also be used, such as flow cytometers with closed chambers, or cuvettes. Additionally, devices such as microfluidic chips with sorting functions may be used in accordance with certain embodiments described herein.

Certain aspects described herein relate to methods for sorting sperm at elevated pressures to achieve improved efficiency, sort speed, and purity, and further relate to methods for offsetting or reducing additional damage imposed on sperm by the elevated pressure. Each of standardizing sperm prior to staining, staining sperm in a single dilution, and changing the position of a catch tube may independently reduce, or perhaps even eliminate, such damage. Some combination of these modifications to existing sorting processes may provide a synergistic benefit.

Obtaining Sperm

Sperm can be obtained, or provided, by virtue of obtaining a sperm sample or sperm solution which contains sperm cells. As used throughout, the term "sperm" refers to the singular or plural of the male reproductive cell, whereas a "sperm sample" refers to carrier fluid in addition to the reproductive cells therein. Examples of sperm samples include neat semen or sperm extended in another solution, such as a sperm extender or buffer. The sperm sample may be in the form of neat semen, extended sperm, frozen-thawed sperm or in combinations thereof. The population of sperm can be obtained at the same location the remaining steps are performed, or can be extended in an appropriate sperm extender for transport to a sorting facility. Once obtained, the sperm can be maintained at room temperature, chilled, or even frozen in an appropriate extender for later use. Sperm for staining and sorting may be acquiring from a mammal, or may be acquired sperm from storage, such as a frozen or chilled straw obtained from storage. Alternatively, frozen or extended sperm may be pooled.

The population of sperm can originate from mammals, such as a non-human mammals listed by Wilson, D. E. and Reeder, D. M., *Mammal Species of the World*, Smithsonian Institution Press, (1993), the entire contents of which are incorporated herein by reference.

At the time of collection, or thawing, or even pooling, sperm may be checked for concentration, pH, motility, and/or morphology. Additionally, antibiotics may be added prior to further processing steps.

Standardizing Sperm

Once obtained, sperm may optionally be standardized to a predetermined concentration and/or towards a predetermined pH. As used herein, "standardizing" may be understood as an action performed in order to bring various characteristics of an ejaculate into a predetermined range or near to said predetermined range. While bovine ejaculates, for example, may vary a great deal in pH and sperm concentration, the step of standardizing sperm concentration or pH, may include the addition of a high capacity buffer which serves to both standardize the pH and buffer against the tendency of ejaculates to become more acidic over time.

Each of the predetermined concentration and pH may be specific to different species, or even to different breeds of animals within a species. In one embodiment, the sperm may be combined with an initial extender in the form of a high capacity buffer, or an extender having a large pH buffering capacity. Exemplary extenders may include TRIS citrate, sodium citrate, sodium bicarbonate, HEPES, TRIS, TEST, MOPS, KMT, TALP, and combinations thereof. Any extender having a buffer with a high capacity for buffering pH may also be employed, and may be used in combination with additional components which promote sperm viability. As an example of an additive, protein may be incorporated in the form of egg yolk, milk, lipoproteins, lecithin, casein or albumin or other protein sources. An energy source may also be incorporated in the form of a monosaccharide such as fructose, glucose, or mannose, or even a disaccharide or trisaccharide. Additionally, antioxidants and antibiotics may be employed in the initial extender to promote sperm viability.

The initial extender may be set at a predetermined pH to standardize the pH of all the obtained sperm samples, such as a pH between about 6.8 and 7.4. In one embodiment, the extender is adjusted to a pH of 7.2. Additionally, semen may become increasingly acidic over time, possibly due to proteins in the seminal fluid, or due to acidic products of metabolism or byproducts of dead or dying cells. The initial extender introduces enough free proton (i.e $H^+$) binding sites to maintain pH near the predetermined target. Even in light of the natural tendency for sperm to become more acidic over time, the initial extender provides a means for stabilizing pH throughout additional processing steps.

The initial extender may contain additives for the purpose of maintaining sperm health. The initial extender may include antibiotics to prevent the proliferation of bacteria. As non-limiting examples, tylosin, gentamicin, lincomycin, linco-spectin, spectinomycin, penicillin, streptomycin, and combinations thereof, may be incorporated into the initial extender.

Antioxidants may also be incorporated into the initial extender for reducing free radicals and oxidative stresses. While the instant discussion relates to the use of antioxidants in an initial extender, it should be appreciated antioxidants may be incorporated into multiple stages of the sperm sorting process, independently or in combination, as described in International Patent Application WO2012167151, the entire contents of which are incorporated herein by reference. A non-limiting list of antioxidants which may be incorporated includes: catalase, SOD, an SOD mimic, glutathione, glutathione reductase, glutathione peroxidase, pyruvate, caproic acid, mercaptoethanol, BHT, lipoic acid, flavins, quinines, vitamin K (and related vitamers), vitamin B12, vitamin B12 vitamers, vitamin E (and related vitamers), tocopherols, tocotrienols, α-tocopheryl, alpha ketoglutarate (AKG), malondialdehyde (MDA), asymmetric dimethylarginine (ADMA) and biologically active derivatives thereof, and combinations thereof.

The concentration of antioxidants may be in the range of 0.01 mg/ml to 0.5 mg/ml, and as non-limiting examples antioxidants listed above may be provided in the concentration 0.01 mg/ml to 5.0 mg/ml; 0.01 mg/ml to 0.25 mg/ml; 0.01 mg/ml to 0.5 mg/ml; 0.01 mg/ml to 1 mg/ml; 0.01 mg/ml to 2.5 mg/ml; 0.01 mg/ml to 5 mg/ml; 0.05 mg/ml to 0.1 mg/ml; 0.05 mg/ml to 1.0 mg/ml; 0.05 mg/ml to 2.5 mg/ml; 0.1 mg/ml to 0.25 mg/ml; 0.1 mg/ml to 0.5 mg/ml; 0.1 mg/ml to 1 mg/ml; 0.1 mg/ml to 2.5 mg/ml; 0.1 mg/ml to 5 mg/ml; 0.15 mg/ml to 0.45 mg/ml; 0.15 mg/ml to 0.5 mg/ml; 0.25 mg/ml to 0.35 mg/ml; 0.25 mg/ml to 0.5 mg/ml; 0.25 mg/ml to 1 mg/ml; 0.25 mg/ml to 2.5 mg/ml; 0.25 mg/ml to 5 mg/ml; 0.35 mg/ml to 0.5 mg/ml; 0.35 mg/ml to 1 mg/ml; 0.35 mg/ml to 2.5 mg/ml; 0.35 mg/ml to 5 mg/ml; 0.5 mg/ml to 1 mg/ml; 0.5 mg/ml to 2.5 mg/ml; 0.5 mg/ml to 5 mg/ml; 1 mg/ml to 2.5 mg/ml; and 1 mg/ml to 5 mg/ml.

As one example, the sperm sample may be diluted in the high capacity buffer in ratios from about 1:1 to about 1:10. The resulting mixture will have a sperm concentration many times below natural sperm concentrations for a particular species. The extended sperm may be centrifuged in order to reconcentrate sperm. Centrifuging the sperm and removing supernatant allows the sperm to be reconcentrated into a predetermined concentration. The predetermined concentration may be selected based on additional sperm processing steps. For example, in the case of sex sorting bovine, sperm may be reconcentrated at between about 2400 million sperm per ml and about 500 million sperm per ml to simulate a natural range of concentrations. Other concentrations, such as between about 1400 million sperm per ml and about 2100 million sperm per ml, or between about 1700 million sperm per ml and about 2100 million sperm per ml may also be achieved for further processing.

Adjusting the sperm concentration and pH may provide a uniform starting point for further processing. For example, a relatively consistent pH and concentration may provide greater predictability in staining sperm, for example with a DNA selective dye. If each sample is adjusted to the same predetermined pH and concentration, fewer trials may be required on each new collection to ensure adequate staining for sex sorting.

A population of sperm will include both X-chromosome bearing sperm and Y-chromosome bearing sperm. Additionally, each of the X-chromosome bearing sperm and the Y-chromosome bearing sperm will include viable sperm and nonviable sperm. Viable sperm can be considered sperm with intact membranes while nonviable sperm can be considered sperm with compromised membranes. The distinction between viable sperm and non-viable sperm in conventional sperm sorting is determined with the inclusion of a quenching dye that permeates membrane compromised sperm. Sperm which tends to be dead or dying absorbs the quenching dye and produces fluorescence signals distinct from the remaining sperm population, whereas sperm having intact membranes tend to be viable and will prevent uptake of the quenching dye. Viable sperm, in the appropriate dosage, will generally be capable of achieving fertilization in an artificial insemination, while nonviable sperm, or membrane compromised sperm, may be incapable of achieving fertilization in an artificial insemination or will have a greatly reduced capacity to do so. However, some sperm capable of fertilization may have compromised membranes, and some sperm with intact membranes may be incapable of fertilization.

Staining Sperm

Whether standardized or not, sperm may be stained with a staining solution for introducing a DNA selective dye. In the staining step, at least a portion of the population of sperm is incubated with a staining solution and a DNA selective fluorescent dye in order to stoichiometrically stain the DNA content of each cell in the sperm population. Hoechst 33342 tends to be less toxic than other DNA selective dyes. The vehicle for delivering this dye may be in the form of a modified TALP buffer adjusted to a pH of about 7.4. Hoechst 33342 is described in U.S. Pat. No. 5,135,759 and is commonly used for this purpose. However, other UV excitable dyes, as well as visible light excitable dyes, fluorescent polyamides, fluorescent nucleotide sequences, and sex specific antibodies could also be used.

Sperm in a natural state is often not readily permeable to such dyes. In order to produce a uniform staining, the first step of staining can include incubating at least a portion of the sperm population at an elevated temperature in a staining solution (sometimes referred to herein as a staining buffer) at an elevated pH in addition to the dye. Examples of appropriate staining solutions can be a TALP, TES-TRIS, TRIS citrate, sodium citrate, or a HEPES based medium, each described in WO2005/095960, incorporated herein by reference. An exemplary modified TALP described in WO2001/37655, incorporated herein by reference, is illustrated in Table 1.

TABLE 1

Modified TALP buffer

| Ingredient | Concentration |
| --- | --- |
| NaCl | 95.0 mM |
| KCl | 3.0 mM |
| NaHPO$_4$ | 0.3 mM |
| NaHCO$_3$ | 10.0 mM |
| MgCL$_2$ 6H$_2$O | 0.4 mM |
| Na Pyruvate | 2.0 mM |
| Glucose | 5.0 mM |
| Na Lactate | 25.0 mM |
| HEPES | 40.0 mM |
| bovine serum albumin | 3.0 mg/ml |

As one example, the population of sperm, or a portion of the population of sperm, could be diluted with the staining solution to between 640×10$^6$ and 40×10$^6$ sperm/ml, to between about 320×10$^6$ and 80×10$^6$ sperm/ml, or to about 160×10$^6$ sperm/ml in the buffer. The DNA selective fluorescent dye can be added to the sperm suspended in the buffer in a concentration of between about 10 µM and 200 µM; between about 20 µM and 100 µM, or between about 30 µM and 70 µM. The pH of the buffer can be between about 6.8 and 7.9; about 7.1 and 7.6; or at about 7.4 in order to help ensure a uniform staining of nuclear DNA. Those of ordinary skill in the art will appreciate the pH can be elevated with the addition of NaOH and dropped with the addition of HCl. Optionally, the previously described antioxidants and concentrations may be incorporated into the staining solution.

The population of sperm can be incubated between 30-39° C., between about 32-37° C., or at about 34° C. The period of incubation can range between about 20 minutes and about three hours, between about 30 minutes and about 90 minutes, or for about 45 minutes to about 60 minutes. As one example, the population of sperm can be incubated for about 45 minutes at 34° C. Even within a single species, sperm concentration and pH and other factors affecting stainability can vary from animal to animal. Those of ordinary skill in the art can appreciate minor variations for incubating sperm between species and even between breeds or animals of the same breed to achieve uniform staining without over staining a population of sperm.

In addition to the DNA selective fluorescent dye, a quenching dye may be applied for the purpose of permeating membrane compromised sperm and quenching the signals they produce. A quenching dye can be understood to include dyes which differentially associate with membrane compromised sperm. It may be that these dyes enter membrane compromised sperm more easily because the membranes are breaking down or otherwise increasingly porous. It may also be that quenching dyes readily enter all sperm membranes and that healthy sperm actively pump quenching dyes out faster than membrane compromised sperm. In either case, the sperm with which the quenching dyes associate includes a large portion of dead and dying sperm, although not necessarily all dead and dying sperm. The quenched signals produced from membrane compromised sperm having an association with quenching dye are distinct enough from the signals of healthy sperm that they may be removed from the further analysis and sorting applied to viable sperm.

In one embodiment, a second staining step is preformed which further reduces the concentration of sperm and introduces the quenching dye. The pH of the second staining solution may be targeted to achieve a target pH in the final sperm sample. Non-limiting examples of two step staining processes are described in published PCT International Application WO 2011/123166 and International Application PCT/US12/58008, the entire disclosure of both are incorporated herein by reference.

In another embodiment, the quenching dye and the DNA selective dye are applied together in a single dilution. In this embodiment, the quenching dye is incubated along with the DNA selective dye at an elevated temperature in the staining solution. As an example, the staining solution may be a modified TALP with a pH of 7.4. However, other stains may be employed including a TES-TRIS, TRIS citrate, sodium citrate or a HEPES based medium having the DNA selective dye and the quenching dye and pH may range between about 7.0 and 7.8. In one embodiment, a synergy may exist when sperm is standardized at an elevated pH of about 7.2 before staining at a pH of 7.4. In this way, the pH to which the sperm is exposed remains in a constant range with minimal variations. Because both the staining solution and the initial extender have high buffering capacities, it is believed the natural tendency of sperm to become more acidic over time will be avoided. Additionally, by minimizing the changes in pH endured by the sperm, it is believed the sperm are in a healthier condition to better face various pressures and stresses endured by sperm in the sex sorting process, including, but not limited to additional stresses and shearing forces induced in flow cytometers operated over 40 psi. Staining sperm in a single dilution may help sperm better survive sorting at elevated sheath fluid pressures, such as sheath fluid pressures greater than 40 psi, sheath fluid pressures between 40 and 65 psi, between 50 and 60 psi, or at about 60 psi.

The stain may be supplemented with an antioxidant in the previously described concentration ranges. In some embodiments, elevated pressures may increase free radicals and oxidative stresses endured by sperm being stained. Accordingly, antioxidants may serve to neutralize free radicals and reduce the oxidative stresses endured by the sperm being stained. A non-limiting list of antioxidants which may be incorporated in the staining process includes: catalase, SOD, an SOD mimic, glutathione, glutathione reductase, glutathione peroxidase, pyruvate, caproic acid, mercaptoethanol, BHT, lipoic acid, flavins, quinines, vitamin K (and related vitamers), vitamin B12, vitamin B12 vitamers, vitamin E (and related vitamers), tocopherols, tocotrienols, α-tocopheryl, alpha ketoglutarate (AKG), malondialdehyde (MDA), asymmetric dimethylarginine (ADMA) and biologically active derivatives thereof, and combinations thereof. Any of the previously described concentrations may be used.

Sorting Stained Sperm

Previously, particle sorting instruments operated for the purpose of sorting sperm relied on the principal of achieving high levels of productivity in terms of sperm sorted per second. However, high efficiency sorting may be performed on such a machine with the goal of recovering as large of a portion of the desired sperm as is possible. Whereas previous focuses on productivity and/or purity failed to achieve significant efficiency with an ejaculate. For example, a MoFlo® XDP, available from Beckman Coulter (Miami Fla., USA) may be set to event rates of about 40,000 events per second, for achieving between about 4,000 and about 8,000 sorts per second, while achieving 90 percent purity. However, higher productivity (sort rates) may be achieved at the expense of one or both of purity and efficiency. In a synergistic combination with improved staining methods, higher sperm concentrations, and lower dead gates provide a vehicle for improving sort rates while maintaining improved sorting efficiency and standard purities. In accordance with certain embodiments, operating pressures and drop drive frequencies may be increased for improving both the purity and efficiency of a sort. A synergistic effect may exist between the combination of certain embodiments described herein. For example, staining and sorting parameters may be modified thereby providing sperm with an improved capacity for fertilization after being subjected to high pressure sorting. Such treatments may permit altered sorting methodologies whereby increased sample and sheath fluid pressures in combination with altered drop drive frequencies result in sorting with improved productivity, improved recovery and improved efficiency.

Whether standardized or not and whether stained in a single step or in two steps, the sperm population can be sorted by a particle sorting instrument, such as flow cytometer. Referring to FIG. 1, a jet-in-air flow cytometer (10) is illustrated, although sorting may be performed with microfluidic chips or other types of flow cytometers, including flow cytometer having closed chambers and cytometers and cytometers incorporating ablating lasers. The flow cytometer (10) includes a cell source (12) for producing a flow of sperm sample, such as a flow of stained sperm sample, for sorting. The rate at which the sperm sample is delivered to the nozzle (14) may be considered the sample flow rate, and may be determined by a sample pressure. The flow of stained sperm sample is deposited within a nozzle (14) and introduced into, or flowed into, a fluid stream (16) of sheath fluid (18). The sheath fluid (18) can be supplied by a sheath fluid source (20) so that as the cell source (12) supplies the sperm into the sheath fluid (18) they are concurrently fed through the nozzle (14). The sheath fluid (18) may be supplied at a sheath flow rate which is determined by a sheath fluid pressure. In this manner the sheath fluid (18) forms a fluid stream coaxially surrounding the sample having stained sperm which exits the nozzle (14) at the nozzle orifice (22). By providing an oscillator (24) which may be precisely controlled with an oscillator control (26), pressure waves may be established within the nozzle (14) and transmitted to the fluids exiting the nozzle (14) at nozzle orifice (22). In response to the pressure waves, the fluid stream (16) exiting the nozzle orifice (22) eventually forms regular droplets (28) at precise intervals. The frequency, and to some extent the shape of the formed droplets may be controlled by a drop drive frequency and drop drive amplitude supplied to the oscillator (24) or the oscillator controller (26).

Each droplet, so formed, retains the sheath fluid and sperm sample that previously formed a portion of the fluid stream (16). Because the stained sperm are surrounded by the fluid stream (16) or sheath fluid environment, the droplets (28) ideally contain individually isolated sperm. However, the sample concentration, sample pressure, and other instrument parameters dictate the frequency with which multiple cells will regularly occupy a single droplet, as well as the percentage of droplets containing sperm.

The flow cytometer (10) acts to sort droplets based on the characteristics of sperm predicted to be contained within the droplets. This can be accomplished through a cell sensing system (30) in communication with an analyzer (36). The cell sensing system (30) includes at least one sensor (32) responsive to the cells contained within fluid stream (16). As one example, two orthogonal PMTs may be incorporated into a sperm sorting flow cytometer for detecting fluorescence at 0 degrees and 90 degrees, although other sensor configurations can readily be employed, such as those described in WO2010/021627, which is incorporated herein by reference.

The cell sensing system (30) provides data to the analyzer (36), which may cause an action depending upon the relative presence or relative absence of a characteristic of cells in the fluid stream (16). Certain characteristics, such as the relative DNA content of sperm, can be detected through excitation with an electromagnetic radiation source (34), such as a laser generating an irradiation beam to which the stained sperm are responsive. The electromagnetic radiation source (34) can be a laser operated at UV wavelength, such as at about 355 nm. An example of such a laser can be a Vanguard 350 (available from Spectra-Physics), which operates at 350 mW. Various optics may be employed to shape the beam profile of the laser, split the beam to more than one stream, or reduce the beam power at a stream. Non-limiting examples of such optics can be found in WO/2004/104178 and WO/2001/85913, each being incorporated herein by reference.

The characteristics of individual sperm, particularly the presence of an X-chromosome or a Y-chromosome can be determined from the detected fluorescence produced in response to the electromagnetic radiation source (34). In particular, configurations of the cell sensing system (30) may be in communication with an analyzer (36) for providing a variety of fluorescence in formation, such as the forward fluorescence of an event, the side fluorescence of an event, or the amount of scatter associated with an event. The analyzer (36) may include written instructions for analyzing the signals produced by the one or more sensors (32) in the cell sensing system (30). The DNA selective fluorescent dye binds stoichiometrically to sperm DNA. Because X-chromosome bearing sperm contain more DNA than Y-chromosome bearing sperm, the X-chromosome bearing sperm can bind a greater amount of DNA selective fluorescent dye than Y-chromosome bearing sperm. Thus, by measuring the fluorescence emitted by the bound dye upon excitation, it is possible to differentiate between X-bearing spermatozoa and Y-bearing spermatozoa. Distinctions, such as sperm which is viable or not viable, may be differentiated in addition to oriented and unoriented sperm by the analyzer (36) according to sorting logic incorporated gating regions.

In order to achieve separation and isolation based upon stained sperm characteristics, emitted light can be detected by the sensor (32) and the information fed to an analyzer (36) coupled to a droplet charger which differentially charges each droplet (28) based upon the characteristics of the stained sperm contained within that droplet (28). In this manner the analyzer (36) acts to permit the electrostatic deflection plates (38) to deflect droplets (28) based on whether or not they contain the appropriate particle or cell.

As a result, the flow cytometer (10) acts to separate stained sperm by causing the droplets (28) containing sperm to be directed to one or more collection containers (40). For example, when the analyzer differentiates sperm based upon a sperm characteristic, the droplets entraining X-chromosome bearing spermatozoa can be charged positively and thus deflect in one direction, while the droplets entraining Y-chromosome bearing spermatozoa can be charged negatively and thus deflect the other way, and the wasted stream (that is droplets that do not entrain a particle or cell or entrain undesired or unsortable cells) can be left uncharged and thus collected from an undeflected stream into a suction tube or the like. Alternatively, one of the X-chromosome bearing sperm or the Y-chromosome bearing sperm may be collected, while the other is discarded with waste.

A controller (42) may form a portion of the analyzer (36) or may be a component external to the analyzer (36). The illustrated controller (42) may also represent a collection of individual controllers. The controller (42) may receive signals or instructions from the analyzer (36) and in response may modify one or more instrument parameters, such as the sample flow rate, sample pressure, sheath flow rate, sheath fluid pressure, drop drive frequency, or drop drive amplitude and the like. The controller (42) may also provide an interface for operator input to manually adjust the sample flow rate, sample pressure, sheath flow rate, sheath fluid pressure, drop drive frequency, drop drive amplitude and the like. The analyzer (36) may include written instructions for modifying the instrument parameters in response to measured sorting parameters, or modifications to instrument parameters may be manually performed by an operator adjusting various settings. The modifications to instrument parameters may be carried out in the analyzer (36) such as for changing sorting logic, abort logic, sorting regions, or gate regions and other parameters specific to making sort decisions in the analyzer. Additional modifications to instrument parameters may be effected by a controller (42), for controlling various external components to the analyzer, such as for controlling the sample pressure, sample flow rate, sheath fluid pressure, sheath flow rate, drop drive frequency, and drop drive amplitude.

Figure 2:
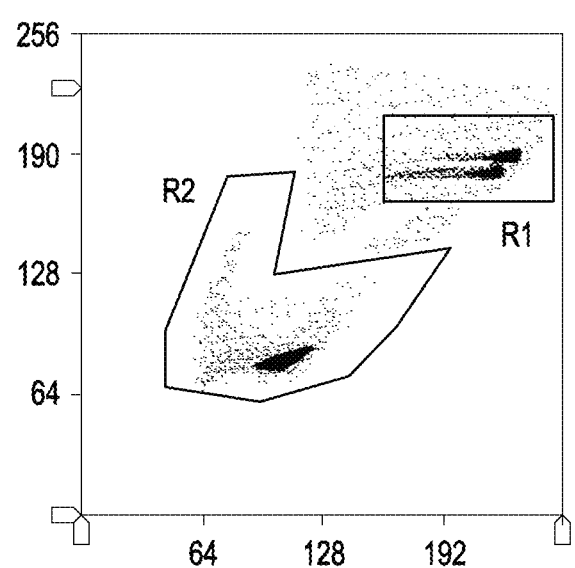
FIG. 2 illustrates a graphical representation of sort parameters acquired in a flow cytometer while sorting sperm according to various embodiments described herein.

FIG. 2 illustrates a representative bivariate plot of side fluorescence and forward fluorescence from a jet-in-air flow cytometer of stained sperm, which may be generated by an analyzer (36). The visual representation of data may be used by an operator to receive feedback relating to the sample undergoing sorting and to graphically demonstrate certain aspects of the current sorting logic. R1, for example, can be seen as a gating region which may be applied to the sort logic of the flow cytometer. Additional numerical output may be provided in a display of the analyzer (36). Such numerical output may be in the form of measured sorting parameters, such as an event rate, an abort rate, sort rate, sorting efficiency, or the percentage of particles in any region or gate. R1 is illustrated as a region which may be considered the live oriented region, because the boundaries of R1 include two dense populations of cells which reflect a closely related X-chromosome bearing population of sperm and Y-chromosome bearing population of sperm. R2 is a gating region set around the non-viable sperm, or the membrane compromised sperm whose fluorescence is quenched by a quenching dye. While a variety of sort logics may be employed, two strategies relating to R1 and R2 might be a first step in a sorting logic whereby all events falling in R1 are accepted for further processing or gating. Alternatively, all events falling outside of R2 are accepted for further processing or gating.

Figure 3:
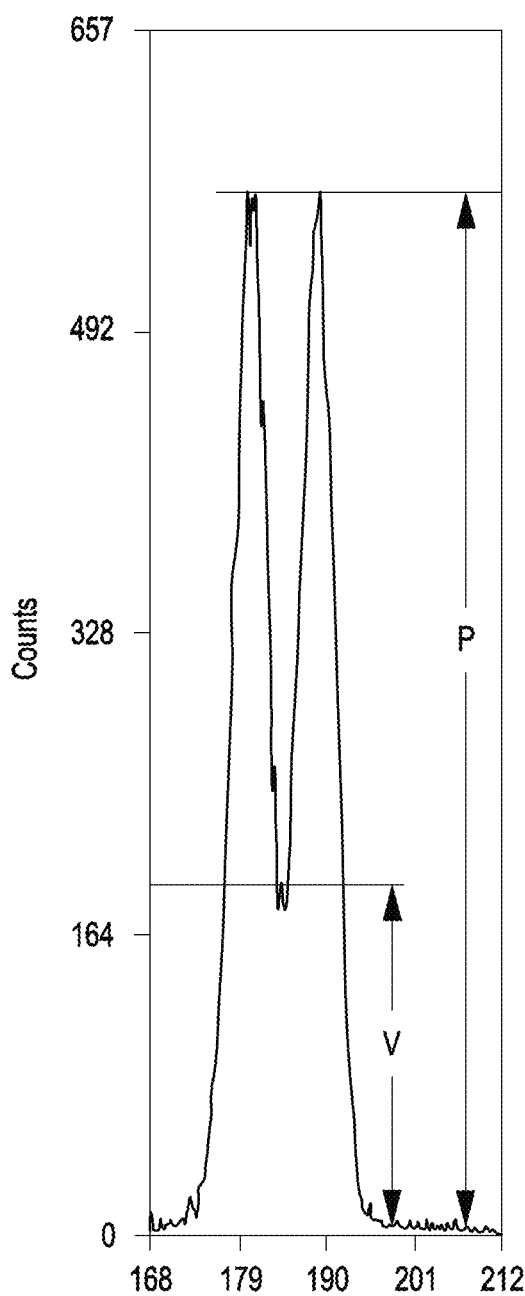
FIG. 3 illustrates a graphical representation of sort parameters acquired in a flow cytometer while sorting sperm according to various embodiments described herein.

FIG. 3 illustrates a univariate plot in the form of a histogram that may be produced by the analyzer (36) and generated into a graphical presentation for an operator. The data illustrated in FIG. 3 may represent the number of occurrence of peak signal intensities from the side or forward fluoresce within a certain period. In the case of sperm, X-chromosome bearing sperm and Y-chromosome bearing sperm tend to have peak intensities that vary by between 2 and 5%, depending on the species, and this difference is reflected in the bimodal distribution of peak intensities seen in FIG. 2. Because X-chromosome bearing sperm and Y-chromosome bearing sperm tend to have differing fluorescence values, each of the peaks represents either X-chromosome bearing sperm of Y-chromosome bearing sperm. Based on the sort logic applied within the analyzer (36), the population of cells in the histogram may be only those cells which were determined to be viable oriented cells, such as those falling into R1 in FIG. 2, or they may represent cells which were not determined to be dead or undesirable, such as every event except those falling in R2. A variety of sorting parameters may be derived from the information contained within this histogram. For example, the level of distinctiveness between the two peaks may provide an indication of what a sorted purity may look like. FIG. 3 further illustrates relative intensity measurements at the lowest point between the two groups, which may be considered a value V and a second relative intensity at the peak or peaks of the histogram at P. A visual inspection of a histogram may provide an operator with an idea of how a flow cytometer is performing, but computer executed instructions for determining a P value, a V value, and a ratio of V to P has not been implemented in commercial sperm sorters. The valley to peak ratio, may be determined as a measured sorting parameter periodically during the course of sorting. The valley to peak ratio, while not the necessarily completely determinative of sorting purities, may provide a means for quickly estimating purity values, either automatically by the execution of written instruction in the analyzer (36), or manually by visual inspection of an operator. Alternatively, the inverse relationship, namely a peak to valley ratio, provides similar information as the inverse value.

Figure 4:
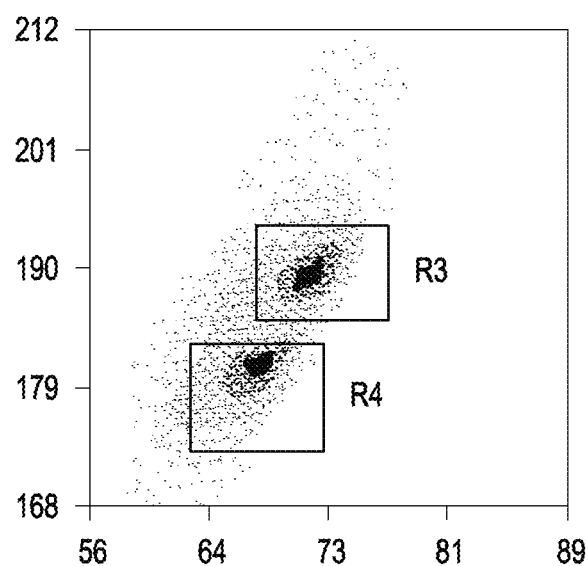
FIG. 4 illustrates a graphical representation of sort parameters acquired in a flow cytometer while sorting sperm according to various embodiments described herein.

Turning to FIG. 4, a second bimodal plot may be generated by the analyzer (36) in response to signals acquired by the cell sensing system (30). The bimodal plot may represent a first axis illustrating the peak intensity value of a forward fluorescence signal or the peak intensity of side fluorescence signal. Like FIG. 3, the data illustrated in FIG. 4 may be gated such that only events falling within R1 in FIG. 2 are included. Alternatively, in the case of sperm, all events which do not fall into the dead gate R2 may also be displayed.

R3 may represent an X-sort gate for collecting X-chromosome bearing sperm. The term X-sort gate may be used interchangeably herein with the term X-gate. With reference to FIG. 4, it may demonstrate how changing the dimensions of the gating regions may affect efficiency, purity, and productivity. If the R3 region were to be expanded, it could be seen that every second more sperm would be sorted as X-chromosome bearing sperm resulting in higher sorting efficiency and higher productivity. However, the expansion of the R3 gate or region would begin to include events having an increasing likelihood of being Y-chromosomes bearing sperm. In order to increase the sorted purity of sperm, the R3 region can be made smaller and/or moved away from the Y-chromosome region. As fewer events fall within the X-sort gate, fewer sperm are sorted in the X-chromosome bearing sperm population and those which are have a greater probability of actually being X-chromosome bearing sperm, meaning the collected purity may be increased. However, both the efficiency, in terms of cells collected, and the productivity, in terms of sorts per second, will decrease as fewer events fall within the R3 region and more coincident events are aborted. Additionally, as other instrument parameters are modified, the illustrated graphs of FIG. 2, FIG. 3, and FIG. 4 may change in shape and nature. For example, increasing a sample pressure or a sample flow rate may result in a reduction in the valley to peak ratio, or may otherwise lessen the bimodal distinction between X-chromosome bearing sperm and Y-chromosome bearing sperm.

Improving Sorting Efficiency and/or Productivity

Figure 5:
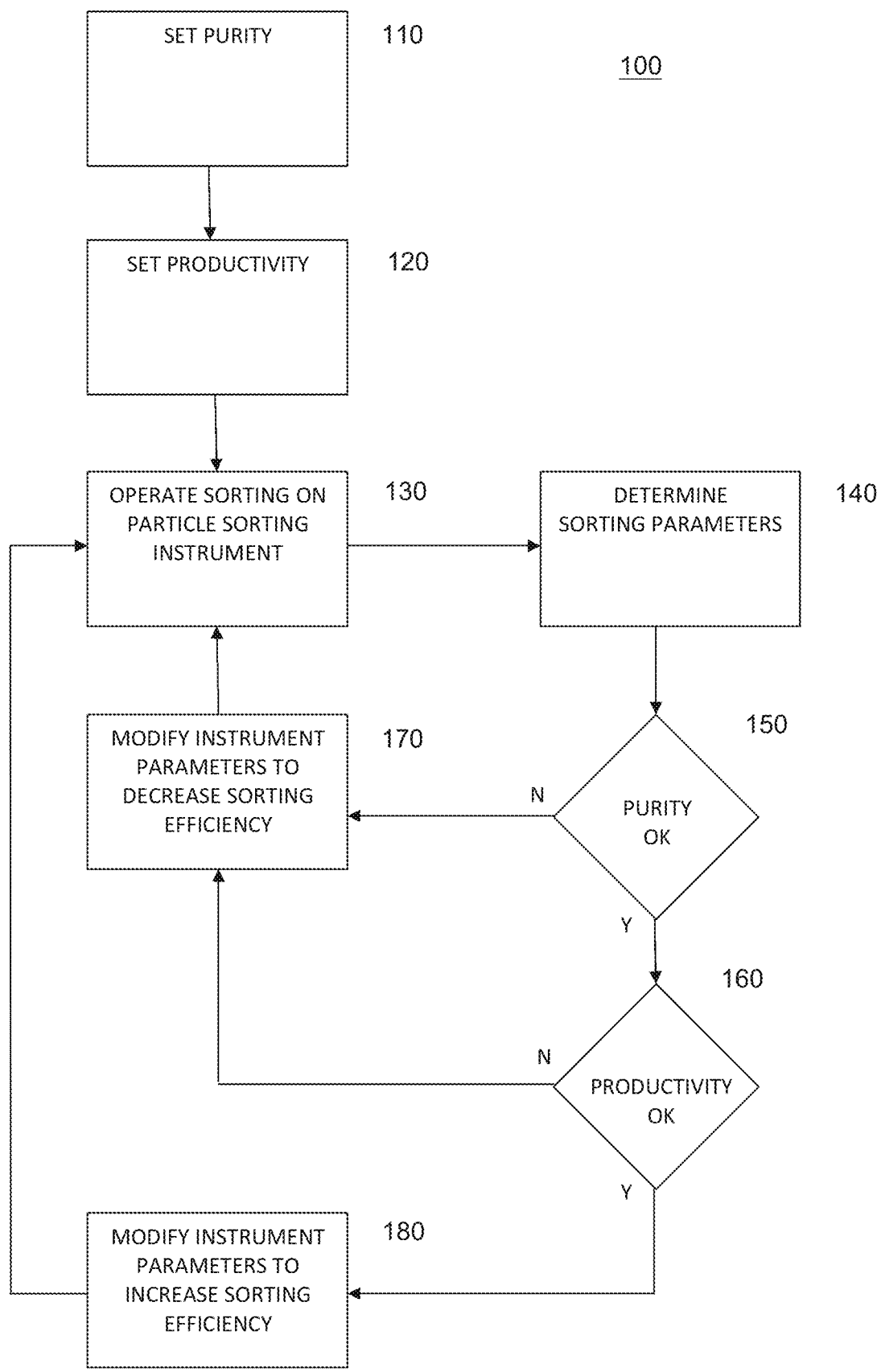
FIG. 5 illustrates a flow chart of a method in accordance with certain embodiments described herein.

Turning to FIG. 5, a method (100) of efficiently sorting sperm is illustrated in the form of a flow chart, which may optionally be employed with other aspects of this disclosure. The method may begin with the step of setting a purity (110), which may be a minimum threshold purity. The minimum purity threshold may be set by an operator based on an expected performance of a particle sorting instrument as well as based on the expected performance of a particular ejaculate, or a particular animal. Alternatively, a minimum purity threshold may be established after a sample has been partially analyzed or sorted. The minimum purity threshold may be entered into the analyzer (36) for comparison against various measured sorting parameters, or may be maintained by an operator, for making manual adjustment to the particle sorting device based on measured sorting parameters. The minimum purity threshold may be may be set at about 86%, at about 87%, at about 88%, at about 89%, at about 90%, at about 91%, at about 92%, at about 93%, at about 94%, at about 95%, at about 96%, at about 97%, at about 98%, or at about 99%.

The productivity may be set (120) before the purity is set, after the purity is set, or at the same time. The productivity may be determined in terms of sorts per second and may be set as a minimum productivity threshold. It should be appreciated that sperm samples which are stained in a manner that reduces the number of dead sperm and are sorted at increased concentrations may be sorted at particularly high productivities. Further increases in productivity may be achieved by expanding sort regions and reducing the minimum purity threshold.

The minimum productivity threshold may be set at about 3,000 sorts per second, 3,500 sorts per second, about 4,000 sorts per second, about 4,500 sorts per second, about 5,000 sorts per second, about 5,500 sorts per second, about 6,000 sorts per second, about 6,500 sorts per second, about 7,000 sorts per second, about 7,500 sorts per second, about 8,000 sorts per second, about 8,500 sorts per second, about 9,000 sorts per second, about 9,500 sorts per second, about 10,000 sorts per second, about 10,500 sorts per second, about 11,000 sorts per second, about 11,500 sorts per second, about 12,000 sorts per second, about 12,500 sorts per second, about 13,000 sorts per second, about 13,500 sorts per second, or about 14,000 sorts per second.

Once each of the purity and the productivity minimum thresholds are set, a particle sorting instrument may begin, or continue the operation of analyzing and sorting particles (130). In the course of operation sorting parameters may be determined (140). The sorting parameters may include those conditions relating to sorting preformed in a particle sorting instrument. Sorting parameters may include measured sorting parameters, parameters which are determined offline, parameters estimated by an operator, and conditions relating to a sorted population of particles or cells. Measured sorting parameters may be determined in the analyzer (36) and can include those conditions relating to sorting measured directly, calculated, or determined in a particle sorting instrument while analyzing and/or sorting a population of particles or cells, such as the event rate, sort rate, sorting efficiency, abort rate, dead gate percentage, live oriented gate percentage, valley to peak ratio, or the percentage of events in other sorting gates, such as an X-sort gate or a Y-sort gate.

A purity for comparison to the minimum purity threshold may be estimated by an operator based on the graphical representations generated by the analyzer, such as illustrated in FIG. 2, FIG. 3, and FIG. 4. A purity may also be determined offline, such as in a subsequent purity analysis of sperm nuclei. The purity may also be estimated with the execution of written instructions on a computer readable media in the analyzer (36). The analyzer (36) may evaluate measured sorting parameters, such as the valley to peak ratio to estimate the purity. An algorithm for estimating purity may incorporate empirical data based on previous valley to peak ratios coordinated with purities subsequently determined offline from sonicated sperm (tailless sperm or sperm nuclei).

The productivity determined in the analyzer (36) may be compared from the measured sorting parameters directly against the minimum productivity threshold (160). In the event both the purity and productivity, however determined, are above their respective minimum threshold values, one or more instrument parameters may be adjusted to increase sorting efficiency (180). The instrument parameters may be adjusted manually by an operator, or the analyzer may execute written instructions automatically for varying the sample pressure, the sample flow rate, or one or more sorting regions. As one example, where purities are determined to be well over the minimum purity threshold.

As one example, the sort logic may be adjusted. The sort logic may be considered the logic applied by the analyzer (36) to determine which cells are sorted and which are discarded with waste. The sort logic may include an abort logic which determines when coincident events will be aborted in the course of sorting. For example, when a high purity is desired, every coincident event may be aborted, whereas when high productivity is desired an abort logic which accepts coincident events may be applied. Depending on the frequency and accuracy with which purity is determined, a percentage of coincident events may also be accepted.

As another example, sorting gates or sorting regions may be modified. When both the purity and the productivity are above their respective thresholds, sorting gates, such as the live gate illustrated in FIG. 2 as R1 may be enlarged to include more events. Similarly, the X-sort gate illustrated in FIG. 4 as R3, the Y-sort gate illustrated in FIG. 4 as R4, or both may be enlarged to sort more particles.

In one embodiment, a change to the drop drive frequency may reduce the number of coincident events by producing more droplets in a given time period and with fewer droplets having more than one cell. Similarly the drop drive amplitude may be modified.

In one embodiment, the sample flow rate may be modified when the minimum purity threshold and minimum productivity are met. In order to increase sort efficiency the sample pressure, or correspondingly the sample flow rate, may be reduced. Such a reduction in sample flow rate increases efficiency by reducing the number of coincident events and improving cell alignment and orientation. Accordingly, in order to further improve efficiency, the sort regions may be expanded while reducing the sample pressure or sample flow rate.

The fluid flow rate in combination with the concentration of cells in the sample together directly affect the measured parameter of the event rate. The measured parameter of the event rate may then be targeted to improve sorting efficiency. The event rate may be targeted between 2,000 and 20,000 events per second at standard concentrations of sperm, such as a sperm sample between 75 and 100 million sperm per ml. At high concentrations of sperm, such as 150 million sperm per ml and greater, event rates may be targeted between 2,000 events per second and 35,000 events per second, or higher. In one embodiment, an increased sample and sheath fluid pressure and increased drop drive frequency may permit even higher event rates while maintaining a targeted sorting efficiency.

In the event either the purity and productivity, however determined, are below their respective minimum threshold values, one or more instrument parameters may be adjusted to decrease sorting efficiency, or to increase either the purity or productivity (170). The instrument parameters may be adjusted manually by an operator, or the analyzer may execute written instructions automatically for varying the sample pressure, the sample flow rate, or one or more sorting regions.

As one non-limiting example, when the productivity minimum threshold is exceeded, but the purity minimum threshold is not, the sample flow rate may be reduced, or one or more of the live oriented sort region (R1) or the X-sort gate (R3) or Y-sort gate (R4) may be decreased to include fewer events, including those events which tend to be outside the required purity. Similarly, in the event the abort logic had been operating in a coincidence accept mode, it may be switched to a coincided reject mode, or to a mode which rejects an increased percentage of coincident events. In the event the minimum purity threshold is met, but the minimum production threshold is not, one or more sort regions may be increased in size to include more events.

After any modifications, the particle sorting instrument may continue to operate and sorting parameters may continue to be determined. Adjustments may then proceed to incrementally improve or maximize the sorting efficiency. Optionally, the incremental adjustments towards a maximum sorting efficiency may stop once either the purity or the productivity approaches a predetermined margin of their respective minimum thresholds.

Figure 6:
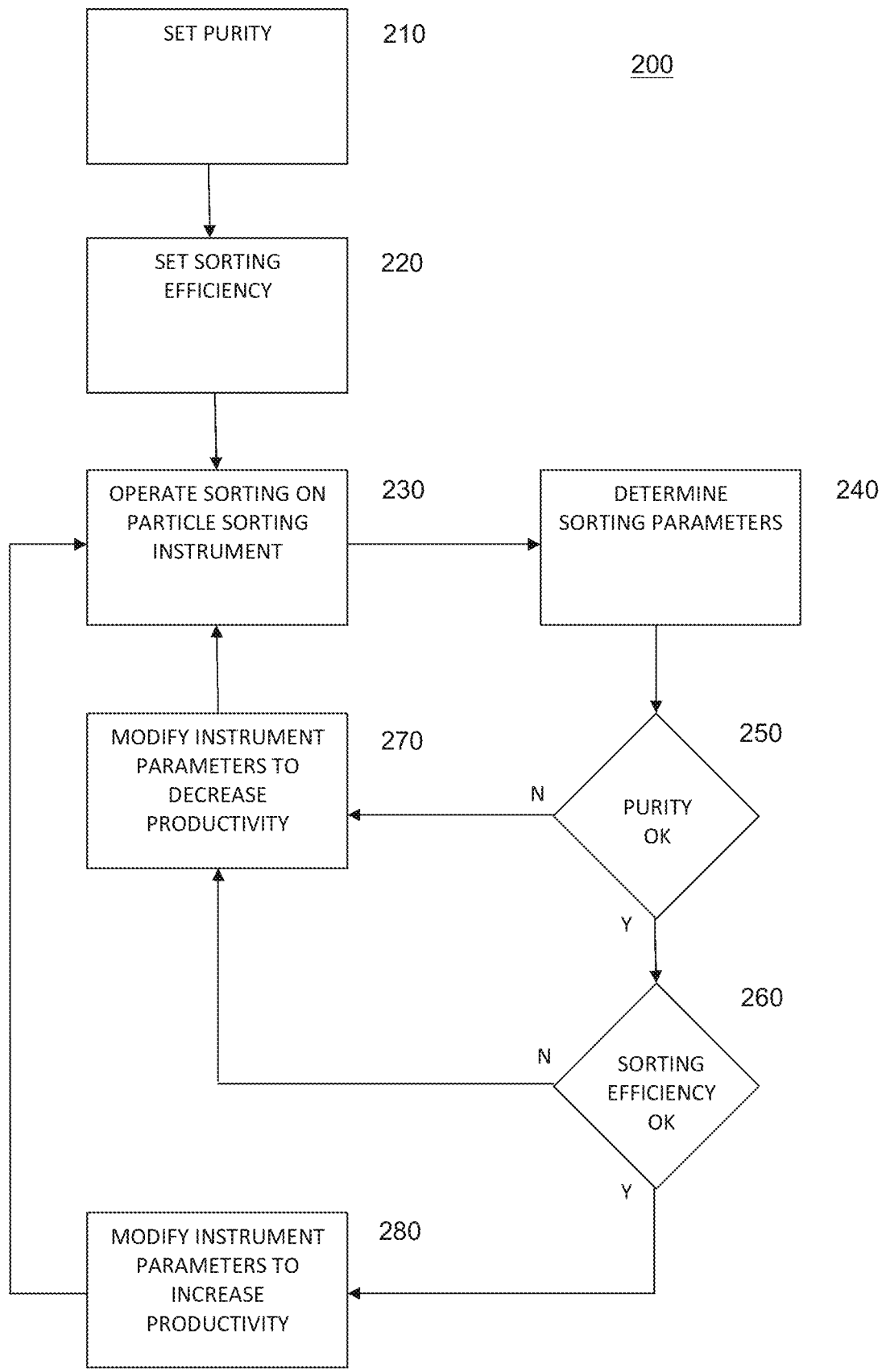
FIG. 6 illustrates a flow chart of a method in accordance with certain embodiments described herein.

Referring to FIG. 6, a method (200) of efficiently sorting sperm, while maximizing productivity is illustrated in the form of a flow chart, which may optionally be implemented with other aspects of the present disclosure. The method may begin with the step of setting a purity (210), which may be a minimum threshold purity. The minimum purity threshold may be set by an operator based on an expected performance of a particle sorting instrument as well as based on the expected performance of a particular ejaculate, or even a particular animal. Alternatively, a minimum purity threshold may be established after a sample has been partially analyzed or sorted. The minimum purity threshold may be entered into the analyzer for comparison against various measured sorting parameters, or may be maintained by an operator, for making manual adjustment to the particle sorting device based on measured sorting parameters. The minimum purity threshold may be set at about 86%, at about 87%, at about 88%, at about 89%, at about 90%, at about 91%, at about 92%, at about 93%, at about 94%, at about 95%, at about 96%, at about 97%, at about 98% or at about 99%.

A sorting efficiency may be set (220) before the purity is set, after the purity is set, or at the same time. The sorting efficiency may be determined in terms of the percentage of sperm sorted or collected over a period of time relative to the total population of sperm analyzed during that period of time. The sorting efficiency may also be determined in terms of a yield on live cells. For example, the sorting efficiency may be determined as the percentage of cells sorted or collected over a period of time relative to the population of cells not considered to be dead or non-viable (i.e. every cell outside the R2 region seen in FIG. 2).

Once each of the purity and the sorting efficiency minimum thresholds are set a particle sorting instrument may begin, or continue, the operation (230) of analyzing and sorting particles. In the course of operation sorting parameters may be determined (240). The sorting parameters may include those conditions relating to sorting preformed in a particle sorting instrument. Sorting parameters may include measured sorting parameters in addition to parameters which are determined offline, estimated by an operator, and conditions relating to a sorted population of particles or cells. Measured sorting parameters may be determined in the analyzer (36) and can include those conditions relating to sorting measured directly, calculated or determined in a particle sorting instrument while analyzing and/or sorting a population of particles or cells, such as the event rate, sort rate, sorting efficiency, abort rate, dead gate percentage, live oriented gate percentage, valley to peak ratio, or the percentage of events in other sorting gates, such as an X-sort gate or a Y-sort gate.

A purity for comparison to the minimum purity threshold (250) may be estimated by an operator based on the graphical representations generated by the analyzer, such as illustrated in FIG. 2, FIG. 3, and FIG. 4. A purity may also be determined offline, such as in a subsequent purity analysis of sperm nuclei. The purity may also be estimated with the execution of written instructions in the analyzer (36). The analyzer (36) may evaluate measured sorting parameters, such as the valley to peak ratio to estimate the purity. An algorithm for estimating purity may be developed from empirical data based on previous valley to peak ratios coordinated with purities subsequently determined offline from sonicated sperm (e.g. tailless sperm or sperm nuclei).

The sorting efficiency determined in the analyzer (36) may be compared from the measured sorting parameters directly against the minimum sorting efficiency threshold (260). In the event both the purity and sorting efficiency, however determined, are above their respective minimum threshold values, one or more instrument parameters may be adjusted to increase productivity (280). The instrument parameters may be adjusted manually by an operator, or the analyzer may execute written instructions automatically for varying the sample pressure, the sample flow rate, or one or more sorting regions.

As one example, the sort logic may be adjusted to increase productivity. The sort logic may be considered the logic applied by the analyzer (36) to determine which cells are sorted and which are discarded with waste. The sort logic may include an abort logic which determines when coincident events will be aborted in the course of sorting. For example, when a high purity is desired, every coincident event may be aborted, whereas when high sorting productivity is desired an abort logic which accepts coincident events may be applied. Alternatively, a percentage of coincident events may also be accepted.

As another example, sorting gates or sorting regions may be modified. When both the purity and the sorting efficiency are above their respective thresholds, sorting gates, such as the live gate illustrated in FIG. 2 as R1 may be enlarged to include more events in order to increase productivity. Similarly, the X-sort gate illustrated in FIG. 4 as R3, the Y-sort gate illustrated in FIG. 4 as R4, or both may be enlarged to sort more particles.

In one embodiment, a change to the drop drive frequency may reduce the number of coincident events by producing more droplets in a given time period and with fewer droplets having more than one cell. Similarly the drop drive amplitude may be modified.

In one embodiment, the sample flow rate may be modified when the minimum purity threshold and minimum sorting efficiency thresholds are met. In order to increase productivity the sample pressure, or correspondingly the sample flow rate, may be increased. Such an increase in sample flow rate increases the number of events per unit time, possibly at a cost to efficiency and a slight cost to purity. In order to further improve productivity and sort efficiency, albeit at a cost to purity, the sort regions may be expanded while increasing the sample pressure, or sample flow rate. In a related embodiment, the sheath fluid pressure and the drop drive frequency may both be increased to improve both the efficiency and the purity of the sorting process.

The fluid flow rate in combination with the concentration of cells in the sample directly affect the measured parameter of the event rate. The measured parameter of the event rate, may then be targeted to improve sorting efficiency while maximizing productivity. The event rate may be targeted between 2,000 and 20,000 events per second at standard concentrations of sperm, such as sperm sample between 75 and 100 million sperm per ml. At high concentrations of sperm, such as 150 million sperm per ml and greater, event rates may be targeted between 2,000 events per second and 35,000 events per second, and higher. At elevated pressures, even higher event rates may be targeted.

In the event either the purity and sorting efficiency, however determined, are below their respective minimum threshold values, one or more instrument parameters may be adjusted to decrease productivity, or to increase either the purity or sorting efficiency (270). The instrument parameters may be adjusted manually by an operator, or the analyzer may execute written instructions automatically for varying the sample pressure, the sample flow rate, or one or more sorting regions. Alternatively, certain instrument parameters may be adjusted which increase both the productivity and sorting purity or efficiency. For example, the sheath fluid pressure and drop drive frequency may be adjusted to increase the separable events, as well as resolution, resulting in improvements in efficiency and productivity, and perhaps even purity.

As a non-limiting example, when the sorting efficiency minimum threshold is exceeded, but the purity minimum threshold is not, the sample flow rate may be reduced, or one or more of the live oriented sort region (R1) or the X-sort gate (R3) or Y-sort gate (R4) may be decreased in size or shifted to include fewer events, effectively excluding more events which tend to be outside the required purity. Similarly, in the event the abort logic had been operating in a coincidence accept mode, it may be switched to a coincided reject mode, or to a mode which rejects an increased percentage of coincident events. In the event the minimum purity threshold is met, but the minimum sorting efficiency threshold is not, one or more sort regions may be increased in size or shifted to include more events, including more events which are less likely to meet the purity threshold.

After any modifications, the particle sorting instrument may continue to operate and sorting parameters may continue to be determined. Adjustments may then proceed to incrementally improve or maximize the productivity. Optionally, the incremental adjustments towards a maximum productivity may stop once either the purity or the sorting efficiency approaches a predetermined margin of their respective minimum thresholds.

Various modifications to the method described in FIG. 5 and FIG. 6 may be implemented in order to accommodate different animals. In the case of bovine, a young genomic sire may have a lower sperm count as compared to more mature animals. The minimum purity threshold and/or productivity threshold may be adjusted accordingly to achieve an efficient use of sperm.

High Pressure Sorting

Sexed semen provides a valuable tool in many agricultural businesses. However, certain inefficiencies in the sperm sorting process often make it infeasible to sort high value sperm, such as sperm from bulls having high genetic value or exotic animals. In the case of sperm sorted to produce male progeny (Y-chromosome bearing sperm), anywhere from 15-20% of the sperm in an ejaculate may be packaged into the final product as straws of sorted sperm, while the remaining sperm is discarded as waste or otherwise lost in the process. In contrast, semen from animals having lower valued ejaculates is readily available (in the case of bovine), high numbers of straws can be produced without concern for the amount of sperm discarded in the process. As task specific software and associated computing capacities improve, modifying flow cytometer operating parameters remains one of the few viable options for improving sort speeds and sorting efficiency.

Operating a flow cytometer having a 70 μm nozzle exit orifice at a sheath fluid pressure of 40 psi allows the formation of up to about 70,000 droplets per second. Depending on the concentration of sperm in the sample, the sorter may run at 35,000 events per second at this pressure, and such event rates may be characterized as high productivity or high throughput sorting. When 70,000 droplets are formed per second, every other droplet would ideally entrain sperm. However, sperm is introduced into these systems in an asynchronous fashion, creating processing conflicts that result in aborting potential sorts.

A number of methods may be employed to manipulate sorting rates. In the case of sorting sperm, sorting rates may be increased significantly by changing the gating logic. Increasing gate sizes for live sperm and for X or Y chromosome bearing sperm decreases the number of events which are discarded as waste but also decreases the purity of the sorted population. Similarly, when a sorter event rate is increased, the resolution of the cell population is decreased causing the subpopulations to increasingly overlap placing greater uncertainty on the sex of those sperm in the overlap. One problem with running higher event rates is that more than 80% of the ejaculate is wasted due to the limitations of this process. In order to achieve high speed, high purity, high efficiency sorting there needs to be more droplets available and the sperm sample must stain well and provide a high number of cells that are oriented and provide quality resolution between the X and Y sperm. This means the sperm sample, differing perhaps by individual sperm sources, must be affinitive to the process of staining with Hoechst 33342.

Conversely, reducing the event rate to about 25,000 events per second, or perhaps even as low as 10,000 events per second, will decrease the conflicts, and the resulting aborts, by increasing, on average, the asynchronous distance between sperm. As one example, this may be accomplished by reducing selection gates for live sperm and for X or Y chromosome bearing sperm, thereby increasing the number of events which are discarded as waste but also increasing the purity of the sorted population. While such a strategy permits fewer aborts and more accurate decisions, the reduced event rate also results in a significant reduction in productivity in terms of the number of sperm sorted in a given time.

Application specific software control programs provide means for producing sorted populations of sperm faster and more efficiently. However, these new processing capabilities which allow for higher event rates, higher performance and higher efficiency are still limited by the number of droplets produced.

From a theoretical perspective, increasing the drop drive frequency provides fewer conflicts while maintaining the same event rate. However, in practice the drop drive frequency is tied to other instrument parameters including the size of the nozzle exit orifice and the sheath fluid pressure. In particular, a negative influence on the quality of the deflected fluid stream starts to manifest at frequencies just above 70 khz in a flow cytometer having a nozzle orifice of 70 μm which is operated at a sheath fluid pressure of 40 psi. Accordingly, any attempt to increase the number of droplets available by virtue of an increase in the drop drive frequency at that pressure results in poor stream quality leading to spraying and sperm damage. As such, and in accordance with industry standards for sorting sperm, most sorters operate between 60,000 and 70,000 droplets per second for sorting at 40 psi, with a 70 μm nozzle orifice. Increasing the system pressure to about 60 psi allows operation at droplet frequencies of about 85,000-95,000 droplets per second. This number of droplets provide nearly ⅓ more droplets to sort, reducing the number of conflicts created by the asynchronous nature of sperm samples. This increase in droplet formation would provide both improved efficiency in terms or reducing aborts, improved purity and improve productivity in terms of sorts per second.

However, since the acceptance and commercial development of sperm sorting operating pressures have been reduced from 50 psi to 40 psi. In the mid 1990's 50 psi was established and implemented for sperm sexing. Work done by Schenk and Suh reported that 40 psi provided higher fertility rates in field trials than the 50 psi standard, thereafter, pressure was reduced (High pressure flow cytometric sorting damages sperm, Theriogenology 2005 Sep. 15:64(5) 1035-48). Since this work, semen sexing has been performed at 40 psi across the industry. Accordingly, as used throughout this disclosure "elevated pressure" may be understood as a sheath fluid pressure greater than 40 psi. As a non-limiting examples, elevated pressure may be considered sheath fluid pressures between 40 psi and 75 psi, or between 50 psi and 65 psi.

Calibrating a Flow Cytometer for High Pressure Sorting

Surprisingly, a new calibration method may place sperm at a different location within droplets ensuring the sperm tail is fully encapsulated, or at least nearly fully encapsulated within the droplet, by placing the head of the sperm slightly in front of the central location of the droplet. Such a placement of the sperm may help sperm better survive high pressure sorting. In standard cell sorting, current calibration methodologies tends to place the head of the sperm in the center of the droplet, or as close thereto as possible. FIG. 7A illustrates a bead (B) placed in the center (302) of a droplet (304) at the break-off point (310) taken the moment the droplet (304) is breaking away from the fluid stream. Prior calibration methods utilize either beads or sperm nuclei.

When an instrument calibrated with the bead (B) of FIG. 7A is supplied with live sperm (S), it can be seen the head (306) of the sperm tends to be aligned in the center (302) of the droplet and the tail (308) is located close to the trailing edge (312) of the droplet allowing the tail to be located in, or interfere with, the neck of the fluid stream. Sperm heads (306) contain the nuclear DNA of sperm in a space of about 10 μm and are the only portion which associate with the DNA selective dyes used for sex sorting. Accordingly, the sperm heads (306) are the only portion of a sperm which fluoresce during sorting, or at the least the sperm head provides the vast majority of the detected fluorescence during sorting. For bovine, the sperm tail (308) may add an additional 80-90 μm in length, the position and location of which is not tracked in a flow cytometer because the DNA selective dye does not associate with the tail.

Sperm tails have an effect on the ability to provide an acceptable stream quality. This is especially important when sorting at a higher pressure and at droplet formation frequencies which produce slightly smaller but relatively similar droplet sizes. For example, a droplet formed at a sheath fluid pressure of 60 psi and a drop drive frequency of 85 khz may be 20% smaller than a droplet formed at sheath fluid pressure of 40 psi and drop drive frequency of 65 khz. Because higher frequencies and higher pressures, for a given nozzle orifice diameter, produce smaller droplets, it is believed, the former methodology resulted in a high occurrence of sperm tails being placed in locations at, or even outside, the back of a droplet which damaged sperm during sorting. FIG. 7C provides an illustration of a sperm (S) located in the droplet with the sperm head (306) located in the leading edge (314) of the droplet (304). This position of the sperm head (306) provides more leeway for the tail (308) at the center (302) and in the trailing edge (312) of the droplet (304). As will be described in further detail, calibrating a flow cytometer instrument with live sperm, as opposed to sperm nuclei or beads, in combination with method steps described below provides empirical feedback. Changing the placement of the sperm tail (308) with this new calibration method allows sperm to be sorted at pressures of 60 psi and higher, thereby providing a method of calibrating a flow cytometer for more efficient and productive sperm sorting.

While sperm are generally described as asynchronous in the fluid stream, pressure waves or other physical phenomena associated with droplet formation tend to create a "train" of sperm. The spacing of this "train" of sperm allows droplet frequency and droplet phase to be manipulated such that the location in sperm in the last forming droplet may be manipulated.

Figure 8:
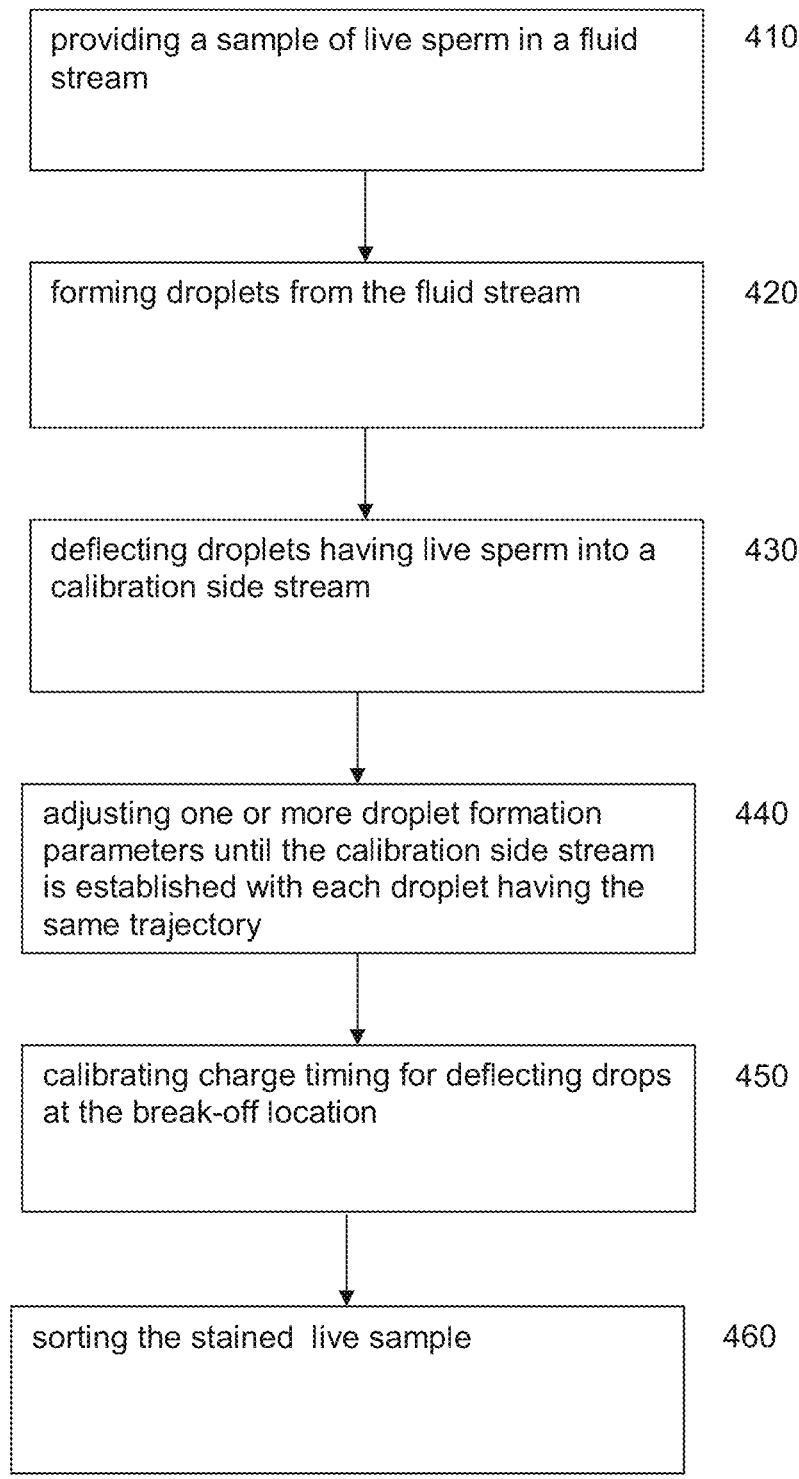
FIG. 8 illustrates a flow chart of a method of calibrating a flow cytometer in accordance with certain embodiments described herein.

FIG. 8 illustrates a flow chart of a method for calibrating a flow cytometer instrument that enables high pressure sperm sex sorting on the flow cytometer instrument (400). At step (410), a sample of live sperm is formed into a fluid stream with a sheath fluid. The sample may be provided at a predetermined concentration in a fluid stream at a predetermined pressure through a nozzle orifice. It should be appreciated "live sperm" is intended in this instance to be distinguished from sperm nuclei, or sonicated sperm heads, and that "live sperm" may include a wide range of motility and viability characteristics, even sperm having viability approaching 0, or even sperm considered membrane compromised with the use of quenching dyes. The sample of live sperm may be provided by a cell source, like the one previously described in FIG. 1. The predetermined concentration may be the same concentration as will be used for sorting sperm once the instrument is calibrated. It may further be appreciated the sperm sample may be in the form of an extended sperm sample stained with a DNA selective dye. As a non-limiting example the stained sperm may have a concentration between $75\times10^6$ sperm per ml and $400\times10^6$ sperm per ml. Similarly, the sheath fluid pressure utilized during the operation of the flow cytometer may be the same value used during calibration. As an example, the sheath fluid pressure may be between 40 psi and 120 psi. As those in the field of flow cytometry may appreciate, at certain pressure levels additional modifications may be necessary for some machines, sample tubes and the like. Certain high pressures described may even exceed the practical capabilities and/or recommended operating pressure of some sorting machines. For example, many sorters are able to sort up to 100 psi but high pressure high frequency may only be typical when sorting very small particles such as bacteria which would not have any negative impact on stream quality due to their very small size.

At step (420), droplets are formed from the fluid stream which entrain the stained sperm. As described with respect to FIG. 1, droplet formation depends on a number of droplet formation parameters including a drop drive voltage having a drop drive amplitude, drop drive frequency and a drop drive phase. At step (430), a calibration side stream is formed by the deflection of droplets into a trajectory spatially separated from stream of non-sorted droplets, as described in FIG. 1. For calibration purposes, X-chromosome bearing sperm may be deflected, Y-chromosome bearing sperm may be deflected, all live sperm may be deflected, or all sperm including dead or dying sperm, or even only dead sperm may be deflected.

At step (440), the calibration side stream is established, one or more of the drop drive amplitude, drop drive phase, or the drop drive frequency are adjusted until a calibration side stream is established without spraying and provides a single quality stream. These adjustments may be made manually on analog equipment, or may be made through a computer interface which controls the drop drive signal. In one embodiment, a flow cytometer have included therein written instructions on a computer readable medium. When in a calibration mode, the execution of these instructions may provide for the automated adjustment of one or more of the drop drive amplitude, drop drive phase, and the drop drive frequency until a calibration side stream is established without spraying and provides a single quality stream. A side stream produced without spraying may be considered a "quality side stream" which indicates that each sorted event is deflected onto the same trajectory for collection or that each droplet has a low variation in individual droplet trajectory. In the case of sperm sorting, the quality side stream indicates that sperm and sperm tails are not interfering with the break off of forming droplets from the stream and that sperm are instead fully encapsulated within the forming droplets.

Sperm can be described as moving asynchronously in the fluid stream of a flow cytometer, or at with irregular spacing, but the sperm are headed in the same direction at this same velocity. As such, droplet frequencies and phases may be empirically searched with live sperm to arrive at a synergistic droplet formation conditions. By utilizing live sperm to empirically establish these droplet formation conditions, a sorter can be calibrated in a manner that tends to place sperm slightly in the leading edge of the droplet, not centered such as standard setups do. Further, it appears that the oscillation used to create droplets may cause sperm spacing which is not completely asynchronous.

Matching the "train" of cells and their order to a specific frequency at the last attached droplet location and the use of the optimized strobe phase, allows one to use a smaller droplet at higher frequency rates and properly position sperm in that droplet at the most optimal time in terms of generating a droplet, charging that droplet and sperm landing at a "optimized" location within the droplet during a sort. Once the quality side stream is achieved, then the drop delay timing calibration is performed. Thus, in one embodiment, the drop drive phase and the drop drive frequency may be said to be empirically established for a tendency to place the head of sperm in the forward portion, or leading edge, of droplets. In one embodiment, the drop drive phase and the drop drive frequency may be said to be empirically established for a tendency to place the tail of the sperm fully within the formed droplet.

At step (450), a drop delay may be determined. The drop delay may be determined by sweeping several drop delays or by other known manual or automated techniques known in the field of flow cytometry. A technique for determining the drop delay may incorporate performing test sorts into multiple puddles on a slide at varying delay timing points. In a course sweep, a number of live sperm may be sorted into puddles on a slide. A recovery percentage may then be determined in terms of the number of sperm in each puddle divided by the number of sorting events for that puddle. Surprisingly, in the case of sperm, additional information may be determined from the shapes of the puddles. As a secondary verification to the test stream quality, it has been determined, when sperm tails interfere with the side stream, a single puddle may resemble two puddles, or a split puddle, or may have an elongated shape. In contrast, when the side stream has a good stream quality and each droplet is put on the same trajectory, a single round puddle is formed. As such, one embodiment may include the step of re-verifying side stream quality by inspecting puddles formed on a slide during step of setting the drop delay. Finally, at step (460), a sperm sample may be sorted in a flow cytometer with the calibrated conditions.

The method described in FIG. 8, which requires adjustment to frequency, amplitude and phases of sorting signals of live sperm, provides a methodology to calibrate a flow cytometer recognizing the effects of sperm with tails on the side stream quality. Applicants realized an improvement in sorting by virtue of empirically eliminating side stream spray before droplet delay calibration is completed. One benefit of this improvement is that sperm better survives high pressure sorting thereby allowing sorting conditions, such as increased pressure, with vastly improved productivity and/or efficiency while minimizing additional damage to the sperm. The method of FIG. 8 provides a solution to a unique problem presented by sperm during flow sorting.

Existing cytometry protocols recommend the use of plastic alignment beads in making drop delay calibrations. The beads are round and are 8-10 um in diameter, which is similar to the size of a bovine sperm head. These beads, however, do not have tails and are not motile. Industry wide, the former method of setting up a sort was to establish the shortest break off point by manipulation of the frequency that produces a strong harmonic that provides the shortest break off point. The operator would set then the droplet reference point on a video monitor and perform a drop delay calibration with the camera showing the reference point of calibration for future intervention during the sorting process. Applicants have found that by abandoning the former principals of establishing the shortest break off point, and instead calibrating the droplet formation to provide clean side streams without spray and to providing sperm heads located in the leading edge of droplets, when calibrated with live sperm, pressures could be moved outside the limitations which have been assumed and followed industry wide.

Calibrating a flow cytometer with live sperm allows sperm sorting without spraying side streams at a wide range of pressures. In the case of higher pressure sorting, it believed this is accomplished by empirically determined settings which tend to place the sperm head slightly towards the leading edge of the droplet. In other words, the sperm are slightly off center increasing the number of sperm with tails that are fully encased within the droplet. Once a good side stream is established the strobe phase may be adjusted to give the image of a correct neck attachment. In the 60 psi setup, when adjusting the drop drive frequency and the drop drive phase for an appropriate stream quality, the neck connecting the last attached droplet is typically either thicker or detached. Previous methodologies may unduly limit adjustments to the drop drive frequency and drop drive phase at the expense of side stream quality. At higher pressures the poor side stream quality may be exacerbated.

The position of the catch tube may be moved to increase the distance to the catch fluid as an alternative methodology to help sperm better survive sorting at increased pressure. As an example, a standard sex sorting operation may employ a 50 ml catch tube having a conical bottom, sometimes referred to as a centrifuge tube. When filled with 3.5 ml of catch fluid and placed in a holder directly under the nozzle of a MoFlo®, the standard distance from the bottom of the MoFlo® deflection plate to the catch fluid level in the catch tube is generally right at about 4.5 inches. By cutting away a portion of the flow cytometer work bench, the distance to the catch fluid may be increased in order to offset damage which may be imposed on sperm when droplets impact the catch fluid with additional velocity imposed by elevated sheath fluid pressures. Alternatively, the catch fluid level may be moved in a synergistic combination with certain methods of calibrating flow cytometers described herein, or with the standardization and one step sorting. As one example, the method may include the step of setting a catch fluid distance based on the sheath fluid pressure setting, based on an animal's historic response to sorting, or perhaps even based on the species or even the breed of animal to be sorted.

As previously described, current industry standards are based on the belief that high pressures are detrimental to sperm health as reported in High pressure flow cytometric sorting damages sperm, Theriogenology 2005 Sep. 15:64(5) 1035-48. However, the damage described may have in fact been caused by spraying that occurred due to sperm location within the droplet rather than the effects of pressure on sperm health.

Example 1—Standardizing Sperm Samples and One Step Staining

Collection—

Sperm was collected from five different bulls on a routine collection schedule using an artificial vagina. Each bull was collected two or three times in one day. Of the five bulls, two were Jersey bulls and three were Holstein bulls. All ejaculates contained greater than 60% progressive motility and sperm concentration varied from 857 million sperm per mL to 2480 million sperm per mL. Ejaculates collected from the same bull were pooled then divided into nine sperm samples for collection and staining treatments.

Sperm Processing and Staining—

Portions of each bull ejaculate were processed and stained by nine different methods, each described as follows.

(A) Control (no standardization, two step staining)—A control was established which did not include the step of standardizing collected ejaculates and in which the sperm was stained in two steps. Prior to staining, the sperm samples were concentrated to between 1700 million sperm per mL and 1800 million sperm per mL by centrifugation or by the addition of a tris-egg yolk extender having a pH of 6.8, depending on the samples starting concentration.

Sperm in the control group was diluted to $160 \times 10^6$ sperm per ml in a modified TALP buffer, as described in Table 1, at a pH of 7.4. Each sperm sample in the control group was then incubated with 16-17 µL of Hoechst 33342 per ml (64-68 µM) of sample for 45 minutes at 34° C. After incubation, an equal volume of a second modified TALP was added reducing the concentration to $80 \times 10^6$ sperm per mL. The second modified TALP includes the components described in Table 1 with the addition of 4% egg yolk, 50 µM yellow food dye No. 6 (20 g/L) and the pH was dropped to 5.5 with the addition of HCl.

(B) Extended (no standardization, two step staining)—In the second group, sperm was not standardized, but was extended with an extender having 20% egg yolk. The sperm was then concentrated to between 1700 million sperm per mL and 1800 million sperm per mL in the same manner described with respect to group (A). The sperm was then diluted to $160 \times 10^6$ sperm per ml in a modified TALP buffer, and stained in the same two step manner described in group (A).

(C) One Step I (no standardization, one step staining with 1% egg yolk)—In a third group sperm was collected and the concentration was adjusted in the same manner as the control group (A). Each sperm sample was then diluted to $160 \times 10^6$ sperm per ml in a modified TALP buffer at a pH of 7.4. The modified TALP buffer was substantially identical to the buffer described in Table 1, except that it additionally included 1% egg yolk and yellow food dye No. 6 at a concentration of 25 µM. Each sperm sample in this group was then incubated with 14-15 µL of Hoechst 33342 per ml (56-60 µM) for 45 minutes at 34° C. After incubation, sperm remained at a concentration of $160 \times 10^6$ sperm per ml.
(D) Standardized I (standardized with 3% egg yolk extender, two step staining)—In this group sperm was standardized by adjusting both the pH and sperm concentration prior to staining and sorting. After collection sperm was diluted 1:3 in an initial extender having a pH of 7.2 as well as a high capacity for buffering pH. The high capacity buffer was supplemented with 3% egg yolk. All samples were then centrifuged to bring the sperm concentration down to between 1700 million sperm and 1800 million sperm per mL. The standardized sperm was then stained according to the two step method described in (A).
(E) Standardized II (standardized with 10% egg yolk extender, two step staining)—In this group sperm was standardized by adjusting both the pH and sperm concentration prior to staining in the same manner described in group (D), except that the initial extender was 10% egg yolk.
(F) One Step and Standardized I (standardized with 3% egg yolk extender, one step staining with 1% egg yolk)—In this group sperm was standardized by adjusting both the pH and sperm concentration prior to sorting in the same manner described in group (D). The standardized sample was then stained with a one step staining process as described in group (C).
(G) One Step and Standardized II (standardized with 10% egg yolk extender, one step staining with 1% egg yolk)—In this group sperm was standardized by adjusting both the pH and sperm concentration prior to staining in the same manner described in group (E). The standardized sample was then stained with a one step staining process as described in group (C).
(H) One Step and Standardized III (standardized with 3% egg yolk extender, one step staining with no egg yolk)—In this group sperm was standardized by adjusting both the pH and sperm concentration prior to staining in the same manner described in group (D). The standardized sample was then stained with a one step staining process as described in group (C), except that no egg yolk was added to the one step staining TALP.
(I) One Step and Standardized IV (standardized with 10% egg yolk extender, one step staining with no egg yolk)—In this group sperm was standardized by adjusting both the pH and sperm concentration prior to staining in the same manner described in group (E). The standardized sample was then stained with a one step staining process as described in group (C) except that no egg yolk was added to the one step staining TALP.

Sorting and Data Acquisition—

Each of the stained samples was sorted on a Legacy MoFlo® SX (Beckman Coulter, USA) with a Genesis digital upgrade (Cytonome/ST, Boston Mass., USA). Those samples which were stained in a two step process were sorted at the concentration of $80 \times 10^6$ sperm per mL, and those samples which were stained by the one step process were sorted at the concentration of $160 \times 10^6$ sperm per mL. Data logged by the flow cytometer was recorded, including information relating to the sort rates and gating of sperm subpopulations. For example, the percentage of sperm gated as dead, as well as the percentages of sperm gated as live-oriented and over ranges were recorded and averaged for the five bulls.

Results—

A comparison of the percentage of sperm which was orientated, unoriented and dead as determined by the sort parameters established in the flow cytometer are summarized in Table 2 below.

TABLE 2

| | % Oriented | % Non-oriented | % Dead | Sort Rate | Overrange |
|---|---|---|---|---|---|
| A) Control | 58.29% | 18.02% | 16.89% | 3500 | 4.32% |
| B) Extended | 60.54% | 20.20% | 8.71% | 3400 | 10.36% |
| C) One Step I | 61.04% | 17.96% | 12.31% | 3500 | 5.65% |
| D) Standardized I | 52.78% | 18.14% | 9.71% | 2900 | 24.73% |
| E) Standardized II | 55.20% | 18.70% | 6.04% | 3200 | 23.44% |
| F) One Step + Standardized I | 57.33% | 20.35% | 5.39% | 3200 | 16.17% |
| G) One Step + Standardized II | 59.99% | 18.89% | 5.19% | 3600 | 16.83% |
| H) One Step + Standardized III | 62.67% | 22.02% | 6.97% | 3800 | 6.23% |
| I) One Step + Standardized IV | 63.49% | 23.16% | 5.61% | 4100 | 5.38% |

As compared to the control (A), the groups One Step I (C), Standardized I (D), and Standardized II (E), each exhibited significantly lower dead populations with reductions of 4.58%, 7.18% and 10.85%, respectively. Based on these improvements, the steps of standardizing sperm samples before staining and modifying the staining process to a single step independently improve the ability of sperm to survive the sorting process. Additionally, One Step and Standardized I (F), One Step and Standardized II (G), One Step and Standardized III (H), and One Step and Standardized IV (I), demonstrate a synergy whereby the combined effect of standardizing an ejaculate and staining the ejaculate in a single step is greater than either improvement individually.

Referring to Table 2, it can be seen that Standardize 1 (D), Standardize II (E), One Step and Standardized I (F), and One Step and Standardized II (G), each appeared to provide significant benefits in terms reducing the number of dead sperm, but the percentage of oriented sperm did not improve. This may be related to the column indicated as over range. While more sperm were gated as live for sorting there appears to be an increase in signals scattered above the sorting gate ranges. This signal may represent sperm which is stuck together or may represent sperm which is bound to egg yolk lipids. In either event, the general pattern emerges that greater quantities of egg yolk reduce dead sperm numbers, but may introduce a new issue and a balance may therefore be required.

Additionally, the each trial incorporating one step staining methodology provided a more efficient means for associating the DNA selective dye Hoechst 33342 with the nuclear DNA of sperm cells. Staining quality was maintained across each tested condition, but the tests including only the single staining step utilized 24, less Hoechst per mL of sample. The ability to stain with less Hoechst may contribute to overall improved sperm health.

Example 2—Standardizing Sperm Samples and One Step Staining

Collection—

Sperm was collected from six different Jersey bulls on a routine collection schedule using an artificial vagina. All ejaculates contained greater than 65% progressive motility and sperm concentration varied from 765 million sperm per mL to 1710 million sperm per mL. Each Sperm sample was divided into two parts in 15 mL tubes for two collection and staining treatments. pH measurements were taken at collection, and at each subsequent processing step.

Sperm Processing and Staining—

Portions of each bull ejaculate were processed and stained by two methods for comparison.

Control (no standardization, two step staining)—A control was established which did not include the step of standardizing collected ejaculates and in which the sperm was stained in two steps. Prior to staining, the sperm samples were concentrated to between 1700 million sperm per mL and 1800 million sperm per mL by centrifugation or by the addition of a tris-egg yolk extender having a pH of 6.8, depending on the samples starting concentration.

Sperm in the control group was diluted to $160 \times 10^6$ sperm per ml in a modified TALP buffer, as described in Table 1, at a pH of 7.4. Each sperm sample in the control group was then incubated with 16-17 µL of Hoechst 33342 per ml (64-68 µM) of sample for 45 minutes at 34° C. After incubation, an equal volume of a second modified TALP was added reducing the concentration to $80 \times 10^6$ sperm per mL. The second modified TALP includes the components described in Table 1 with the addition of 4% egg yolk, 50 µM red food dye No. 40 (20 g/L) and the pH was dropped to 5.5 with the addition of HCl.

One Step and Standardized (standardized with 10% egg yolk, one step staining with one percent egg yolk)—Sperm was standardized by adjusting both the pH and sperm concentration prior to staining. After collection sperm was diluted 1:3 in an initial extender having a pH of 7.2 as well as a high capacity for buffering pH. The high capacity buffer was supplemented with 1% egg yolk. All samples were then centrifuged to bring the sperm concentration down to between 1700 million sperm and 1800 million sperm per mL.

The sperm samples were then diluted to $160 \times 10^6$ sperm per ml in a modified TALP buffer at a pH of 7.4. The modified TALP buffer was substantially identical to the buffer described in Table 1, except that it additionally included 1% egg yolk and yellow food dye No. 6 at a concentration of 25 µM. Each sperm sample in this group was then incubated with 16-17 µL of Hoechst 33342 per ml (64-68 µM) for 45 minutes at 34° C. After incubation, sperm remained at a concentration of $160 \times 10^6$ sperm per ml.

Sorting and Data Acquisition—

Each sample was sorted on a MoFlo® SX (Beckman Coulter, USA) with a Genesis digital upgrade (Cytonome/ST, Boston Mass., USA). The control was sorted at the concentration of $80 \times 10^6$ sperm per mL, while the standardized sperm was sorted at $160 \times 10^6$ sperm per mL. Data was logged by the flow cytometer and then averaged for the 6 bulls.

Results—

TABLE 3 illustrates the recorded pH of both the control (A) and the standardized ejaculate (B). These Values are reflected in TABLE 3 below. While the standardized ejaculate is subject to an initial increase, a subsequent increase is avoided during staining and the following drop off is also avoided. Additionally, TABLE 4 illustrates similar benefits in the reduction of dead sperm that was seen in Example 1. Specifically, the standardized sample which was stained in one step had 5.67% less dead sperm.

TABLE 3

|  | Initial | Before Centrifugation | After Centrifugation | During Staining | After staining | Before cytometer |
|---|---|---|---|---|---|---|
| Control (A) | 6.34 | 6.34 | 6.25 | 7.22 | 7.07 | 6.59 |
| Standardized (B) | 6.34 | 7.12 | 6.85 | 7.18 | 6.98 | 6.98 |

TABLE 4

|  | PV | % Oriented | % Dead | Sort Rate | Duplets/Triplets |
|---|---|---|---|---|---|
| Control | 1.86 | 52.99 | 14.63 | 35.83 | 21.73 |
| Standardized - One Step | 1.97 | 57.22 | 8.96 | 37.00 | 24.59 |
| Difference | 0.11 | 4.23 | −5.67 | 1.17 | 2.86 |

Example 3—Standardizing Sperm Samples and One Step Staining Reduces Dead Sperm

Collection—

Sperm was collected from three different Jersey bulls and three different Holstein bulls on a routine collection schedule for a total of 17 collections. Each ejaculate was divided for two treatments.

Sperm Processing and Staining—

Portions of each bull ejaculate were processed and stained by two methods for comparison.

Control (no standardization, two step staining)—A control was established which did not include the step of standardizing collected ejaculates and in which the sperm was stained in two steps. Sperm in the control group was diluted to $160 \times 10^6$ sperm per ml in a modified TALP buffer, as described in Table 1, at a pH of 7.4. Each sperm sample in the control group was then incubated with 16-17 µL of Hoechst 33342 per ml (64-68 µM) of sample for 45 minutes at 34° C. After incubation, an equal volume of a second modified TALP was added reducing the concentration to $80 \times 10^6$ sperm per mL. The second modified TALP includes the components described in Table 1 with the addition of 4% egg yolk, 50 µM red food dye No. 40 (20 g/L) and the pH was dropped to 5.5 with the addition of HCl.

Standardized III and One Step (standardized with 3% egg yolk extender, one step staining)—The remaining sperm was standardized by adjusting both the pH and sperm concentration prior to staining and sorting. After collection sperm was diluted 1:3 in an initial extender having a pH of 7.2 as well as a high capacity for buffering pH. The high capacity buffer was supplemented with 3% egg yolk. The sperm sample was then diluted to 160×10$^6$ sperm per ml in a modified TALP buffer at a pH of 7.4. The modified TALP buffer was substantially identical to the buffer described in Table 1, except that it additionally included 1% egg yolk and yellow food dye No. 6 at a concentration of 25 μM. Each sperm sample in this group was then incubated with 14-15 μL of Hoechst 33342 per ml (56-60 μM) for 45 minutes at 34° C. After incubation, sperm remained at a concentration of 160×10$^6$ sperm per ml.

Sorting and Results—

The control group was run through a Legacy MoFlo® SX (Beckman Coulter, Miami Fla., US) with a Genesis digital upgrade (Cytonome/ST, Boston Mass., USA) at a concentration of 80×10$^6$ sperm per ml, while the Standardized III and One Step was sorted at a concentration of 160×10$^6$ sperm per ml. Table 5 illustrates the percentage of cells in the dead gate of each ejaculate and the average. After sorting, percentages of sperm occurring in the dead gates (R2 seen in FIG. 3), were indicated for both samples. It can be seen the average over 17 bulls was 17% of the sperm was gated as dead in the control and only 10% of the sperm was gated as dead for the treated sperm, meaning the treatment provided a significant benefit to sperm health.

TABLE 5

| Bull | | Dead Gate (%) | |
|---|---|---|---|
| Ejaculate Number | Bull | CONTROL | ONE-STEP and STANDARDIZED III |
| 01 | Holstein Bull 1 | 16% | 12% |
| 02 | Holstein Bull 2 | 26% | 6% |
| 03 | Jersey Bull 1 | 15% | 7% |
| 04 | Holstein Bull 2 | 19% | 3% |
| 05 | Jersey Bull 1 | 13% | 6% |
| 06 | Holstein Bull 3 | 19% | 12% |
| 07 | Jersey Bull 2 | 25% | 14% |
| 08 | Holstein Bull 1 | 25% | 21% |
| 09 | Holstein Bull 2 | 20% | 20% |
| 10 | Jersey Bull 3 | 9% | 5% |
| 11 | Jersey Bull 2 | 19% | 17% |
| 12 | Holstein Bull 3 | 15% | 14% |
| 13 | Jersey Bull 1 | 10% | 7% |

TABLE 5-continued

| Bull | | Dead Gate (%) | |
|---|---|---|---|
| Ejaculate Number | Bull | CONTROL | ONE-STEP and STANDARDIZED III |
| 14 | Holstein Bull 1 | 9% | 6% |
| 15 | Holstein Bull 1 | 9% | 8% |
| 16 | Holstein Bull 3 | 17% | 6% |
| 17 | Holstein Bull 3 | 16% | 5% |
| | Average | 17% | 10% |

Example 4—Optimizing Sorting Efficiency in Flow Cytometer

Collection and Sorting—

Sperm was collected from a Holstein bull and stained according to the Standardized III and One step protocol described in the Examples 1 and 3. The sample was placed on Legacy MoFlo® SX (Beckman Coulter, Miami Fla., US) with a Genesis digital upgrade (Cytonome/ST, Boston Mass., USA). During sorting, sheath fluid pressure was established at 40 psi and the drop drive frequency was set to 64.9 KHz. The sample pressure was adjusted to target event rates of about 1500, 3500, 7500, 8500, 10,000 15000, 20000, 25000, and 30000.

Results—

Measured sorting parameters from each target event rate were recorded in TABLE 6. The ejaculate in this example demonstrated about a 3%-5% dead gate which allowing for large portions of the sperm to be included in the live oriented gate; between 79.1% and 85.4%. The sorting logic utilized in this sort gated on a live oriented region of sperm (R1). R1 was established by an operator to retain a large portion of sperm. The X-sort gate was similarly established by an operator with a target of 90% purity. Data was periodically digitally logged for several samples at each event rate. Data was averaged at each event rate to provide averages for productivity (Sort Rate), sorting efficiency (Sort Rate/Event Rate), Valley to Peak ratio, abort rate, as well as the percentage of the population in the Dead gate (R2), the percentage of the population in the live oriented gate (R1), the percentage of the population of sperm in the X-Sort gate (R3), and the percentage of viable (live) sperm in the X-Sort Gate. Additionally, purities were determined off line for each sperm sorted at each event rate setting. Purities were determined by sonicating the tails off 1 million sperm and collected at each group of event rates and measurement in an off line purity analyzer. This measurement was performed twice for each group and averaged.

TABLE 6

| | Valley/Peak (%) | Event Rate (Hz) | Sort Rate (Hz) | Sort Rate/Event Rate (%) | Abort Rate (Hz) | Abort Rate/Sort Rate | Dead Gate (%) | Live-Oriented (%) | X-Sort Gate (%) | X-Sort/Viable (%) | X-Purity (%) |
|---|---|---|---|---|---|---|---|---|---|---|---|
| 1 | 67.4% | 1722 | 694 | 40.3% | 48 | 7.0% | 6.4% | 82.9% | 54.1% | 57.7% | 96.0% |
| 2 | 66.6% | 3697 | 1361 | 36.8% | 141 | 10.4% | 4.5% | 84.9% | 52.2% | 54.6% | 96.0% |
| 3 | 63.4% | 7377 | 2591 | 35.1% | 414 | 16.0% | 2.9% | 85.4% | 50.0% | 51.5% | 95.5% |
| 4 | 63.4% | 8515 | 3005 | 35.3% | 522 | 17.4% | 2.7% | 84.9% | 51.2% | 52.6% | 95.5% |
| 5 | 62.1% | 9891 | 3415 | 34.5% | 645 | 18.9% | 2.7% | 84.4% | 51.2% | 52.6% | 96.0% |
| 6 | 54.7% | 16686 | 4774 | 28.6% | 1306 | 27.4% | 2.8% | 82.8% | 47.1% | 48.5% | 93.0% |
| 7 | 51.0% | 19760 | 5080 | 25.7% | 1604 | 31.6% | 2.8% | 81.8% | 44.6% | 45.9% | 91.5% |
| 8 | 47.5% | 24839 | 5822 | 23.4% | 2175 | 37.4% | 2.8% | 80.2% | 43.5% | 44.8% | 90.0% |
| 9 | 43.9% | 29666 | 6332 | 21.3% | 2706 | 42.7% | 3.1% | 79.1% | 42.4% | 43.7% | 92.5% |

It can be seen that low event rates reduce the abort rates and improve sorting efficiency. In particular, the abort rate is 7% of the sort rate when the event rate is 1722.

Additionally the synergistic effect of reducing dead sperm is illustrated by virtue of the fact over 50% of the sperm sample was gated in the X-sort gate for event rates less than 10,000 events per second. The low percentage of dead sperm in combination with the high percentage of live oriented sperm allows gating an R3 region to be adjusted such that R3 encroaches the region of FIG. 5 where sperm have a greater probability of being Y-chromosomes bearing sperm than X-chromosome bearing sperm. Even when slightly encroaching this region, the purity checked post sort remained 96%, even though 54% of all sperm was included in the X-sort gate and 57% of all live sperm was included in the X-sort gate.

The synergistic combination of improved staining techniques in combination with sorting methods which focus on efficiency can be seen to provide reliable sperm sorting methods which may provide between 25% and about 40% yield on the total sperm population, and maintain purities greater than 90%.

One aspect of this disclosure projects more spatially efficient flow cytometers, which may allow more sorting heads in an available space. In such an arrangement, more flow cytometer sorting heads may be dedicated to a single sperm sample, and each one may be operated at an improved efficiency, thereby combining the benefits of efficient sorting methods with high productivity.

Example 5—Improved Efficiency and Productivity at Elevated Pressures and Comparable Viability Sperm Handling—

Semen was collected from five bulls including two Holstein bulls two Jersey bulls and one Simmental bull. At the time of collection, volume, concentration, motility, morphology and pH were checked, then antibiotics were added in accordance with industry practices. Each bull utilized in the example presented motility at or greater than 70%. Semen was then standardized by placement in an extender with a pH buffering capacity and centrifuged for reconcentration between 1700-1800 million sperm per ml. 3 ml of each bull were stained with TALP having Hochest 33342 and a yellow quenching food dye, and the concentrations after staining was 160 million sperm per ml, in accordance the one step staining described in previous examples.

Sperm from each bull was divided into four treatments. Two treatments were performed at 40 psi and two treatments were performed at 65 psi. At each of 40 and 65 psi, one treatment was established as a high productivity treatment and one treatment was established as a high efficiency treatment.

Treatment 1—In the first treatment sorter sheath fluid pressure was set to 40 psi. An event rate of about 35,000 events per second was then established by adjusting the sample pressure. The drop drive frequency and other droplet generations signals were adjusted until a calibration side stream was established without spraying. A drop delay calibration was then performed to determine a charge delay.

Treatment 2—In the second treatment the sorter was maintained at a pressure of 40 psi and the event rate was dropped to about 20,000 events per second with sample pressure adjustments. Gating was then readjusted on the flow cytometer.

Treatment 3—In the third treatment the sheath fluid pressure was set to 65 psi and an event rate of about 35,000 events per second was established with the sample pressure. The drop drive frequency and other droplet generation signals were adjusted until a calibration side stream was established without spraying. A drop delay calibration was then performed to determine a charge delay.

Treatment 4—In the fourth treatment sheath fluid pressure was maintained at 65 psi and an event rate of about 20,000 events per second was established by adjusting the sample pressure. Gating was then readjusted on the flow cytometer.

Sperm Sorting and Freezing—

Sperm from each of the five bulls was sorted under each calibration described. During each sort, data was logged from the flow cytometer, and is seen in TABLE 7. A total of 10 million X-chromosome bearing sperm were collected in a catch tube having an A fraction of extender including about 20% egg yolk for each. Collected sperm was cooled for 90 minutes to about 5 C. B fraction of extender including 12% glycerol was added in two equal portions. After the B fraction was added, the sample was centrifuged and resuspended in an equal part A fraction and B fraction extender having about 20% egg yolk and about 6% glycerol. Multiple 0.25 ml straws were filled for each bull and each treatment and then frozen in liquid nitrogen.

TABLE 7

|  |  | Abort Rate | X Sort Rate | Oriented % | X Gate % | PVR |
| --- | --- | --- | --- | --- | --- | --- |
| Treatment 1 | 40 psi | 2487 | 4490 | 60.38 | 36.77 | 43.82 |
| Treatment 2 | 40 psi | 1188 | 3460 | 63.03 | 38.79 | 52.42 |
| Treatment 3 | 65 psi | 2034 | 6019 | 62.65 | 39.27 | 48.48 |
| Treatment 4 | 65 psi | 982 | 4363 | 65.57 | 41.45 | 57.71 |

Post Thaw—

Frozen straws were selected for each bull and treatment to undergo quality control testing. Motility was checked 0 hours and then again after three hours. Additionally, viability was determined by flow cytometer analysis of a portion of the thawed sperm that was then stained with Sybr Green and propidium iodide. The acrosome health of another portion of thawed sperm was analyzed by flow cytometry with PI/PNA staining. Additionally, sperm from each straw was sonicated and sperm nuclei were analyzed for purity. The results are seen in TABLE 8.

TABLE 8

|  |  | 0 hr Motility | 3 hr Motility | Intact Acrosomes | Viable | Purity |
| --- | --- | --- | --- | --- | --- | --- |
| Treatment 1 | 40 psi | 72 | 50 | 76 | 44 | 92 |
| Treatment 2 | 40 psi | 71 | 48 | 76 | 46 | 94 |
| Treatment 3 | 65 psi | 68 | 45 | 73 | 41 | 92 |
| Treatment 4 | 65 psi | 65 | 47 | 74 | 43 | 92 |

Results—

The data logged in TABLE 7 illustrates several trends, a significant trend being that the slower event rates of treatments 2 and 4 slightly increased the percentage of sperm in the X gate and moderately improved the Peak to Valley ration (PVR) and the percentage of sperm in the oriented gate, as compared to treatments 1 and 3, respectively. Additionally, the increased pressure of treatment 3 and 4 independently decreased the abort rate and further improved the percentage of sperm in the X gate as compared to treatments 1 and 2, respectively.

Example 6—Improved Productivity at an Elevated Pressure, Comparable Viability Under Modified Conditions Sperm Handling—

Semen was collected from seven bulls including four Holstein bulls and three Jersey bulls. At the time of collection, volume, concentration, motility, morphology and pH were checked, then antibiotics were added. Each bull utilized in the example presented motility at or greater than 60%. Semen was then standardized by placement in an extender with a pH buffering capacity and centrifuged for reconcentration between 1700-1800 million sperm per ml. Sperm was stained according to the One Step procedures outlines in Example 1, without the addition of egg yolk at the time of staining.

Sorter Calibration—

A first data set was produced with a Legacy MoFlo® SX having a Genesis digital upgrade available from Cytonome/ST (Boston, Mass., USA) set to an operating sheath fluid pressure of 40 psi. The drop drive frequency was set to the highest frequency providing a good quality side stream within an existing recommended range. The drop delay was then determined with a test sort onto a microscope slide. The initial catch fluid level of a collection tube was positioned 4.5 inches below the deflection plates of the flow cytometer, or which is the standard position of a 50 ml catch tube in a MoFlo® flow cytometer.

A second dataset was produced with the same Legacy MoFlo® SX operating with a sheath fluid pressure at 60 psi. The drop drive frequency was set to the highest frequency providing a good quality side stream within an existing recommended range. The drop delay was then determined with a test sort onto a microscope slide. The initial catch fluid level of a collection tube was positioned 4.5 inches below the deflection plates of the flow cytometer, or which is the standard position of a 50 ml catch tube in a MoFlo® flow cytometer.

A third data set was produced in the same manner as the second data set except that the collection tube was moved downwards 1.25 inches through a cut out in the work bench on which the flow cytometer was located. The initial level of the catch fluid was 5.75 inches below the deflection plates of the flow cytometer.

Sperm Sorting and Freezing—

Sperm from each of the seven bulls was sorted under each calibration described. A total of 15 million X-chromosome bearing sperm were collected in a catch tube having an A fraction of extender including about 20% egg yolk for each.

Collected sperm was cooled for 90 minutes to about 5 C. B fraction of extender including 12% glycerol was added in two equal portions. After the B fraction was added, the sample was centrifuged and resuspended in an equal part A fraction and B fraction extender having about 20% egg yolk and about 6% glycerol. Multiple 0.25 ml straws were filled for each bull and each treatment and then frozen in liquid nitrogen.

Post Thaw—

Frozen straws were later selected for each bull and treatment to undergo quality control testing. Straws were thawed and motility was checked at 0 hours and then again after three hours. Additionally, sperm viability was assessed by flow cytometry after staining with Sybr/PI. Five of the seven bulls were selected for IVF. Additionally sperm from each straw were sonicated and sperm nuclei were analyzed for purity.

Results—

Averaged measured sorting parameters determined by data logging software were compiled for all sorts performed at 40 psi and for all sorts performed at 60 psi. Additionally, the average time to sort 15 million X chromosome bearing sperm at 40 psi was 48:17 and the average time to sort 15 million X chromosome bearing sperm at 60 psi was 34:23.

TABLE 9

|             | Event Rate | Abort Rate | Sort X Rate | Oriented | Dead | X %   | PVR   |
|-------------|------------|------------|-------------|----------|------|-------|-------|
| Avg. 40 psi | 36,595     | 3034       | 5350        | 59.60    | 9.53 | 42.03 | 42.06 |
| Avg. 60 psi | 40,830     | 2822       | 7175        | 60.32    | 9.68 | 43.82 | 46.39 |

The benefits of sorting at 60 psi over 40 psi can readily be seen in terms of productivity, as well as, efficiency in the averaged measured sorting parameters recorded in TABLE 9. With respect to productivity, an average of 7175 sorts per second allowed 15 million sperm to be sorted 13:54 faster. Further 60 psi, provided higher event rates, an improved sperm orientation, and an improved distinction between X chromosome bearing sperm and Y chromosome bearing sperm.

Each of the seven bulls were frozen, a straw for each bull was thawed and evaluated for motility, compromised sperm membranes (Sybr/PI) and purity. Five of the seven bulls, including three Holstein bulls and two Jersey bulls, were selected for IVF. The conversion of oocytes to embryos for each treatment is recorded in TABLE 11.

Additionally, a benefit was realized in changing the distance of the catch fluid, in particular for sorting at 60 psi. TABLE 10 illustrates the average post thaw motilities, viability and purity for each treatment over the five bulls selected for IVF trials.

TABLE 10

|                | 0 Hr | 3 Hr | Viable | Purity |
|----------------|------|------|--------|--------|
| 40 psi - 4.5   | 59   | 38   | 31.66  | 92     |
| 60 psi - 4.5   | 56   | 35   | 30.59  | 94     |
| 60 psi - 5.75  | 65   | 39   | 32.60  | 93     |

Notably for the five bulls evaluated at 60 psi, the standard catch fluid location provided slightly lower post thaw motility and slightly lower viability as compared to sorting at 40 psi in the same location. However, moving the catch tube down an additional 1.25 inches (3.18 cm) provided a 10% improvement in 0 hour motility at 60 psi and an 11% improvement in 3 hour motility. For the five bulls utilized in IVF sperm sorted at 60 psi and collected at the second catch tube position demonstrated motility and viability which was slightly better than sorting at 40 psi.

TABLE 11

|                | Oocytes | Embryos | % Oocytes converted to Embryos |
|----------------|---------|---------|-------------------------------|
| 40 psi - 4.5   | 2004    | 205     | 10.23                         |
| 60 psi - 4.5   | 2062    | 186     | 9.02                          |
| 60 psi - 5.75  | 2081    | 194     | 9.32                          |

Example 7—Modified Extension and Staining Helps Sperm Better Survive High Pressure Sorting Sperm Preparation—

Semen was collected from three bulls including two Jersey bulls and one dairy cross breed. At the time of collection, volume, concentration, motility, morphology and pH were checked, then antibiotics were added in accordance with industry practices. Each bull utilized in the example presented motility at or greater than 70%. Sperm was then stained according to two different treatments.

Two step staining—Depending on the initial sperm concentration of each ejaculate, sperm in a second group was either centrifuged and extended to between 1700 and 1800 million sperm per ml in a TRIS citrate having a pH of 6.8 or directly stained from raw ejaculate. The second group was stained in a first dilution to $160\times10^6$ sperm per ml in a modified TALP buffer, as described in Table 1, at a pH of 7.4. Each sperm sample in the second group was then incubated with 16-17 μL of Hoechst 33342 per ml (64-68 μM) of sample for 45 minutes at 34° C. After incubation, an equal volume of a second modified TALP was added reducing the concentration to $80\times10^6$ sperm per mL. The second modified TALP includes the components described in Table 1 with the addition of 4% egg yolk, 50 μM red food dye No. 40 (20 g/L) and the pH was dropped to 5.5 with the addition of HCl.

One step staining—In a first treatment sperm was standardized by placement in an extender with a pH buffering capacity and centrifuged for reconcentration between 1700-1800 million sperm per ml. Sperm was then stained in a single step by dilution to $160\times10^6$ sperm per ml in a modified TALP buffer at a pH of 7.4. The modified TALP buffer was substantially identical to the buffer described in Table 1, except that it additionally yellow food dye No. 6 at a concentration of 25 μM and an antioxidant. Each sperm sample in this group was then incubated with 14-15 μL of Hoechst 33342 per ml (56-60 μM) for 45 minutes at 34° C. After incubation, sperm remained at a concentration of $160\times10^6$ sperm per ml.

Sperm Sorting—

A Legacy MoFlo® SX (available from Beckman Coutler, Miami, Fla.) with a Genesis digital upgrade available from Cytonome/ST (Boston, Mass.) was utilized to sort both stained samples of sperm according to six different conditions. In each condition, the flow cytometer was calibrated with live sperm an event rate was established at about 40,000 events per second. Eight million sperm were bulk sorted in each condition and data logging information was generated once five million sperm were sorted.

I. In a first condition, the flow cytometer was calibrated with live sperm at a sheath fluid pressure of 40 psi. Then eight million sperm were sorted in to a collection tube placed at a first position. The first position corresponds to the catch fluid level in a 50 ml catch tube being 4.5 inches below the deflection plates of a Legacy MoFlo® SX.

II. In a second condition, the flow cytometer was again operated at a sheath fluid pressure of 40 psi. The collection tube was placed in a second position, corresponding to a catch fluid distance 5.75 inches below the deflection plates of the Legacy MoFlo® SX.

III. In a third condition, the flow cytometer was calibrated with live sperm at a sheath fluid pressure of 65 psi. Eight million sperm were sorted into the catch tube located at the first position, 4.5 inches below the deflection plates.

IV. In a fourth condition, the flow cytometer was operated again at a sheath fluid pressure of 65 psi, but the catch fluid level was moved to the second position 5.75 inches below the deflection plates.

V. In a fifth condition, the flow cytometer was calibrated with live sperm at a sheath fluid pressure of 75 psi. Eight million sperm were sorted into the catch tube located at the first position, 4.5 inches below the deflection plates.

VI. In a sixth condition, the flow cytometer was operated again at a sheath fluid pressure of 75 psi, but the catch fluid position was moved to the second position, 5.75 inches below the deflection plates. Again, eight million sperm were bulk sorted in this condition.

Each group of eight million bulk sorted sperm for each tested conditions landed in a catch tube having an A fraction of extender including about 20% egg yolk. Collected sperm was cooled for 90 minutes to about 5 C. B fraction of extender including 12% glycerol was added in two equal portions. After the B fraction was added, the sample was centrifuged and resuspended in an equal part A fraction and B fraction extender having about 20% egg yolk and about 6% glycerol. French straws (0.25 ml) were then filled for each bull and each treatment and then frozen in liquid nitrogen.

Post Thaw—

Frozen were thawed and then motility was checked 0 hours and then again at three hours, the results being seen in TABLE 12. Additionally, viability and acrosome integrity was flow cytometrically determined at 0 hours post thaw with propidium iodide and PNA stain combination, seen in TABLE 13.

TABLE 12

| | | | 0 hr Motility | 3 hr Motility |
|---|---|---|---|---|
| 40 psi | Position 1 | One step | 70.0 | 55.0 |
| | | Two Step | 62.5 | 47.5 |
| | Position 2 | One step | 66 | 53.5 |
| | | Two Step | 61.5 | 52.5 |
| 65 psi | Position 1 | One step | 45 | 30.0 |
| | | Two Step | 32.5 | 29.0 |
| | Position 2 | One step | 37.5 | 40.0 |
| | | Two Step | 40 | 35.0 |
| 75 psi | Position 1 | One step | 42.5 | 25.0 |
| | | Two Step | 37.5 | 17.5 |
| | Position 2 | One step | 37.5 | 25.0 |
| | | Two Step | 37.5 | 20.0 |

TABLE 13

| | | | Non-Viable | Viable | Intact Acrosomes |
|---|---|---|---|---|---|
| 40 psi | Position 1 | One step | 62.6 | 37.4 | 73.7 |
| | | Two Step | 69.0 | 31.0 | 67.5 |
| | Position 2 | One step | 66.4 | 33.6 | 75.0 |
| | | Two Step | 64.8 | 35.1 | 77.3 |
| 65 psi | Position 1 | One step | 73.8 | 26.2 | 57.1 |
| | | Two Step | 81.9 | 18.7 | 58.3 |
| | Position 2 | One step | 67.5 | 32.6 | 70.9 |
| | | Two Step | 68.3 | 31.7 | 73.1 |
| 75 psi | Position 1 | One step | 76 | 24.1 | 68.5 |
| | | Two Step | 75.3 | 24.7 | 68.1 |
| | Position 2 | One step | 72.6 | 27.4 | 72.2 |
| | | Two Step | 73.3 | 26.7 | 68.4 |

Results—

One of the three bulls presented 3 hour motilities of 22 and less at every tested condition and was removed from further consideration for presenting a quality control failure under even standard conditions. The averages of the two remaining bulls are seen in TABLE 12 and TABLE 13, which illustrate a clear trend that pressures elevated above 40 psi increase sperm damage as evidenced by reduced post thaw motility as well as reduced sperm viability, and to a lesser extend acrosome health. At each pressure, one step staining, either at position 1 or position 2, provided the highest percentage of viable sperm. Further, by adjusting either the position of the catch tube or the staining processes additional damage presented by elevated pressures is reduced. For example, two step staining at position 1, the standard catch tube location, demonstrated 31% viable sperm according to the post thaw PI/PNA flow cytometer analysis. Whereas, at 65 psi, one step staining demonstrated 32.6% viability and two step staining demonstrated 31.7% viability at the adjusted position 2.

At each position, one step staining presented reduced damage when increasing the sheath fluid pressure from 40 psi to 65 psi, as compared to two step staining. At position 1, one step staining provided a 11.2% fewer viable sperm (from 37.4% to 26.2%), whereas at position 1, two step staining provided a 12.3% fewer viable sperm (from 31.0% to 18.7%). In position 2, one step staining demonstrated only 1% fewer viable sperm (from 33.6% to 32.6%), whereas two step staining presented 3.4% fewer viable sperm (from 35.1% to 31.7%). It can be seen from TABLE 13 that both changing the catch distance and performing one step staining independently provide a reduction in sperm damage caused at increased sheath fluid pressures. It can also be seen synergistic combinations may incorporate both modifications to enable sperm to better survive high pressure sorting. For example, one step staining at position two presented a slight increase in the number of viable sperm as compared to two step staining at position 1 (TABLE 13), as well as a comparable 3 hr post that motility (TABLE 12).

As can be easily understood from the foregoing, the basic concepts of the present invention may be embodied in a variety of ways. The invention involves numerous and varied embodiments of sex sorting sperm including, but not limited to, the best mode of the invention.

As such, the particular embodiments or elements of the invention disclosed by the description or shown in the figures or tables accompanying this application are not intended to be limiting, but rather non-limiting examples of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of "sorter" should be understood to encompass disclosure of the act of "sorting"—whether explicitly discussed or not—and, conversely, were there effectively disclosure of the act of "sorting", such a disclosure should be understood to encompass disclosure of a "sorter" and even a "means for sorting." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

Moreover, for the purposes of the present invention, the term "a" or "an" entity refers to one or more of that entity. As such, the terms "a" or "an", "one or more" and "at least one" can be used interchangeably herein.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

We claim:

1. A method of sorting bovine sperm comprising:
   extending a bovine sperm sample in an initial extender at a sperm sample to initial extender ratio between about 1:1 and 1:10 to form an extended bovine sperm sample;
   reconcentrating the extended bovine sperm sample to a concentration between 900 million sperm per ml and 2400 million sperm per ml, wherein the reconcentrated sperm concentration is higher than the sperm concentration following dilution;

staining sperm in the reconcentrated bovine sperm sample with a DNA selective dye; and sorting the stained sperm with a flow cytometer with a sheath fluid pressure between about 45 psi and about 65 psi, wherein the steps of extending and reconcentrating the bovine sperm sample reduces damage imposed on the sperm by the sheath fluid pressure.

2. The method of claim 1, wherein the step of staining is performed with a modified TALP having the DNA selective dye and a quenching dye, a TES-TRIS having the DNA selective dye and a quenching dye, TRIS citrate having the DNA selective dye and a quenching dye, sodium citrate having the DNA selective dye and a quenching dye, or a HEPES based medium having the DNA selective dye and a quenching dye.

3. The method of claim 2, wherein the modified TALP has a pH of between about 7.0 and about 7.8.

4. The method of claim 1, wherein the stained bovine sperm sample is diluted in a staining media to a sperm concentration of: between 80 million sperm per ml and 160 million sperm per ml; between 160 million sperm per ml and 240 million sperm per ml; or between 240 million sperm per ml and 320 million sperm per ml.

5. The method of claim 1, wherein the initial extender comprises one or more selected from the group consisting of: sodium bicarbonate, TRIS citrate, sodium citrate, HEPES, TRIS, TEST, MOPS, KMT, TALP, and combinations thereof.

6. The method of claim 5, wherein the initial extender further comprises an antioxidant.

7. The method of claim 1, further comprising the step of calibrating the flow cytometer.

8. The method of claim 7, wherein the step of calibrating the flow cytometer further comprises producing a calibration side stream and providing each droplet in the calibration side stream which is expected to contain live sperm with a uniform trajectory.

9. The method of claim 7, wherein the step of calibrating the flow cytometer further comprises adjusting instrument parameters so live sperm tend to be placed in a leading edge of forming droplets.

10. The method of claim 7, wherein the step of calibrating the flow cytometer further comprises establishing a calibration side stream with the highest drop drive frequency at which there is no spraying.

11. The method of claim 1, wherein the sheath fluid pressure comprises a pressure in a range: about 50 psi to about 55 psi; about 55 psi to about 60 psi; or about 60 psi to about 65 psi.

12. The method of claim 1, wherein the steps of extending and reconcentrating the bovine sperm sample reduces the additional sperm damage imposed by pressures greater than 40 psi by about 50%, about 60%, about 70%, about 80%, about 90%, or by nearly 100%.

13. The method of claim 1, wherein the step of sorting the stained sperm sample further comprises the step of sex sorting sperm into a viable X chromosome bearing population and/or a viable Y chromosome bearing population.

14. The method of claim 1, wherein the sheath fluid pressure comprises a pressure between about 50 psi and about 60 psi, or at about 60 psi.

* * * * *